(12) United States Patent
Buchanan et al.

(10) Patent No.: US 11,957,465 B2
(45) Date of Patent: Apr. 16, 2024

(54) ACCELERATED ERGONOMIC COLLECTION OF CAPILLARY BLOOD

(71) Applicant: RedDrop Dx, Inc., Fort Collins, CO (US)

(72) Inventors: Kristopher Scott Buchanan, Fort Collins, CO (US); William Kristopher Buchanan, Fort Collins, CO (US); Dirk van den Boom, Encinitas, CA (US); Thomas Michael Johannsen, Centennial, CO (US); Wesley Joseph Hager, Fort Collins, CO (US); Matthew Bryan Huntingdon, Fort Collins, CO (US); Christopher Andrew Frankson, Fort Collins, CO (US); Landon Bruggeman, Fort Collins, CO (US)

(73) Assignee: RedDrop Dx, Inc., Fort Collins, CO (US)

( * ) Notice: Subject to any disclaimer, the term of this patent is extended or adjusted under 35 U.S.C. 154(b) by 0 days.

(21) Appl. No.: 18/110,566

(22) Filed: Feb. 16, 2023

(65) Prior Publication Data

US 2024/0065589 A1    Feb. 29, 2024

Related U.S. Application Data

(63) Continuation of application No. 18/081,475, filed on Dec. 14, 2022, now abandoned.
(Continued)

(51) Int. Cl.
*A61B 5/15* (2006.01)

(52) U.S. Cl.
CPC .. *A61B 5/150061* (2013.01); *A61B 5/150343* (2013.01); *A61B 5/150351* (2013.01)

(58) Field of Classification Search
CPC ........ A61B 5/150145; A61B 5/150206; A61B 5/15117; A61B 5/157; A61B 5/150816;
(Continued)

(56) References Cited

U.S. PATENT DOCUMENTS 8,561,795 B2    10/2013  Schott
8,808,202 B2     8/2014  Brancazio
(Continued)

FOREIGN PATENT DOCUMENTS

EP    3793442 A1    3/2021
EP    3821804 A1    5/2021
(Continued)

OTHER PUBLICATIONS

D.P. Holmes, "Confined Fluid Flow: Microfluidics and Capillarity", Boston University, Short Course, Sapienza, Università di Roma (2015), at p. 20 of pp. 1-123.
(Continued)

*Primary Examiner* — Kaylee R Wilson
*Assistant Examiner* — Huong Q Nguyen
(74) *Attorney, Agent, or Firm* — Kunzler Bean & Adamson; Thomas D. Briscoe

(57) ABSTRACT

Apparatuses, methods, and systems are disclosed for accelerated ergonomic collection of capillary blood. An apparatus and system include a blood collection module with a proximal portion including a vacuum generation chamber, a distal portion including a blood collection chamber, a concave mid portion including a pressure equalization channel configured to equalize reduced air pressure. The apparatus further includes a sealing surface to stably seal the blood collection module to the skin around a collection site and a slide latch actuated by a lengthwise sliding motion. Also included is a lancet carrier with linearly-arranged lancet strips to puncture rows of blood extraction slits in the collection site. The
(Continued)

apparatus also includes an angled transfer port with a low-resistance non-microfluidic blood flow channel to a transfer module, then to a plasma separation module with a multilayer laminate and plasma separation membrane. Methods for accelerated ergonomic collection of capillary blood are disclosed.

17 Claims, 14 Drawing Sheets

Related U.S. Application Data

(60) Provisional application No. 63/400,277, filed on Aug. 23, 2022.

(58) Field of Classification Search
CPC .......... A61B 5/150824; A61B 5/15113; A61B 5/150343; A61B 5/150061; A61B 5/150969; A61B 5/14514; A61B 5/150984; A61B 5/150351; A61M 37/0015

See application file for complete search history.

(56) References Cited

U.S. PATENT DOCUMENTS

| | | | |
|---|---|---|---|
| 8,821,412 | B2 | 9/2014 | Gonzalez-Zugasti et al. |
| 8,827,971 | B2 | 9/2014 | Gonzalez-Zugasti et al. |
| 9,033,898 | B2 | 5/2015 | Chickering, III et al. |
| 9,041,541 | B2 | 5/2015 | Levinson et al. |
| 9,113,836 | B2 | 8/2015 | Bernstein et al. |
| 9,119,578 | B2 | 9/2015 | Haghgooie et al. |
| 9,289,763 | B2 | 3/2016 | Berthier et al. |
| 9,295,417 | B2 | 3/2016 | Haghgooie et al. |
| 9,730,624 | B2 | 8/2017 | Gonzalez-Zugasti et al. |
| 9,775,551 | B2 | 10/2017 | Bernstein et al. |
| 9,987,629 | B2 | 6/2018 | Berthier et al. |
| 10,188,335 | B2 | 1/2019 | Haghgooie et al. |
| 10,426,390 | B2 | 10/2019 | Berthier et al. |
| 10,492,716 | B2 | 12/2019 | Berthier et al. |
| 10,543,310 | B2 | 1/2020 | Bernstein et al. |
| 10,638,963 | B2 | 5/2020 | Beyerlein et al. |
| 10,779,757 | B2 | 9/2020 | Berthier et al. |
| 10,799,166 | B2 | 10/2020 | Gonzalez-Zugasti et al. |
| 10,835,163 | B2 | 11/2020 | Haghgooie et al. |
| 10,870,110 | B2 | 12/2020 | Olson |
| 10,888,259 | B2 | 1/2021 | Jordan et al. |
| 10,932,710 | B2 | 3/2021 | Jordan et al. |
| 10,939,860 | B2 | 3/2021 | Levinson et al. |
| 11,033,212 | B2 | 6/2021 | Berthier et al. |
| 11,177,029 | B2 | 11/2021 | Levinson et al. |
| 11,202,895 | B2 | 12/2021 | Davis et al. |
| 11,253,179 | B2 | 2/2022 | Bernstein et al. |
| 11,266,337 | B2 | 3/2022 | Jackson et al. |
| 11,298,060 | B2 | 4/2022 | Jordan et al. |
| 11,395,618 | B2 | 7/2022 | Berthier et al. |
| 11,399,755 | B2 | 8/2022 | Ivosevic et al. |
| 11,510,659 | B2 | 11/2022 | Berthier et al. |
| 11,523,805 | B2 | 12/2022 | Moga et al. |
| 11,633,136 | B2 | 4/2023 | Welch et al. |
| 11,642,057 | B2 | 5/2023 | Berthier et al. |
| 11,673,133 | B2 | 6/2023 | Berthier et al. |
| 11,697,114 | B2 | 7/2023 | Olson |
| 2003/0050656 | A1* | 3/2003 | Schraga ............... A61B 5/1411 606/182 |
| 2011/0105872 | A1* | 5/2011 | Chickering, III .. A61B 5/14514 600/573 |
| 2012/0156278 | A1* | 6/2012 | Beretta ................ A61J 1/2089 424/443 |
| 2014/0323911 | A1* | 10/2014 | Sloan ................ A61B 5/15003 600/573 |
| 2014/0342371 | A1 | 11/2014 | Holmes |
| 2015/0320349 | A1 | 11/2015 | Haghgooie et al. |
| 2016/0038068 | A1 | 2/2016 | Chickering, III et al. |
| 2016/0174888 | A1* | 6/2016 | Berthier ........... A61B 5/150503 600/573 |
| 2019/0000365 | A1* | 1/2019 | Beyerlein ............... B01L 3/508 |
| 2019/0320960 | A1 | 10/2019 | Olson et al. |
| 2019/0331703 | A1 | 10/2019 | Olson et al. |
| 2021/0048404 | A1* | 2/2021 | Miyazawa ....... A61B 5/150358 |
| 2022/0369957 | A1 | 11/2022 | Nawana |
| 2023/0138274 | A1 | 5/2023 | Vouillamoz et al. |

FOREIGN PATENT DOCUMENTS

| | | |
|---|---|---|
| EP | 4000730 A1 | 5/2022 |
| RU | 2797989 C1 | 6/2023 |

OTHER PUBLICATIONS

Baillargeon, K. R. et al., Microsampling tools for collecting, processing, and storing blood at the point-of-care,. Bioengineering and Translational Medicine, (2023), 1-21, 8.

Cabello, C. M. et al., Membrane-based, sedimentation-assisted plasma separator for point-of-care applications,. Analytical Chemistry, (2013), 220-231, 46.

Collier, B.B. et al., Maximizing Microsampling—Measurement of Comprehensive Metabolic and Lipid Panels Using a Novel Capillary Blood Collection Device, J. Applied Lab. Med., (2023), 1-12.

Durc, P. et al., Fast blood plasma separation device for point-of-care applications. Talanta, (2018), 55-60, 183.

Gonzalez-Suarez, A. M. et al., Automated Microfluidic System with Active Mixing Enables Rapid Analysis of Biomarkers in 5uL of Whole Blood,. Analytical Chemistry, (2022), 9706-9714, 94.

Hara, Y. et al., Fabrication of stainless steel microneedle with laser-cut sharp tip and its penetration and blood sampling performance,. International Journal of Automation Technology, (2016), 950-957, 10.

Menestrina Dewes, M. et al., Evaluation of the Tasso-SST capillary blood microsampling device for the measurement of endogenous uracil levels,. Clinical Biochemistry, (2022), 1-6, 107.Montagu, J.I., et al., Filtering in pre-evacuated containers, (2022). U.S.

Mohammed, T. et al., Evaluation of independent self-collected blood specimens for COVID-19 antibody detection among the US veteran population,. Diagnostic Microbiology and Infectious Disease, (2022), 115770, 104.

Nabatiyan, A. et al., Membrane-based plasma collection device for point-of-care diagnosis of HIV,. Journal of Virological Methods, (2011), 37-42, 173.

Noble, L. D. et al., Painless Capillary Blood Collectiont: A Rapid Evaluation of the Onflow Device. Diagnostics, (2023).

Norton, S. E. et al., A new blood collection device minimizes cellular DNA release during sample storage and shipping when compared to a standard device, Journal of Clinical Laboratory Analysis, (2013), 305-311, 27.

Oka, K. et al., Fabrication of a micro needle for a trace blood test,. Sensors and Actuators, A: Physical, (2002), 478-485, 97-98.

Rincon Pabon, J. P. et al., Fit-for-Purpose Validation of a PK Assay applying Blood Collection by Volumetric Absorptive Microsampling,. Journal of Applied Bioanalysis, (2022), 8.

Skoglund, E. et al., Estimated Clinical and Economic Impact through Use of a Novel Blood Collection Device to Reduce Blood Culture Contamination in the Emergency Department: A Cost-Benefit Analysis,. Journal of Clinical Microbiology, (2019), 57.

Van Eyk, J. E. et al., Precision Medicine: Role of Proteomics in Changing Clinical Management and Care,. Journal of Proteome Research, (2019), 1-6, 18.

Verbaan, F. J. et al., Improved piercing of microneedle arrays in dermatomed human skin by an impact insertion method,. Journal of Controlled Release, (2008), 80-88, 128.

PCT/US2023/030843, "Notification of Transmittal of the International Search Report and the Written Opinion of the International Searching Authority, or the Declaration", International Searching Authority, Dec. 11, 2023, pp. 1-24.

* cited by examiner

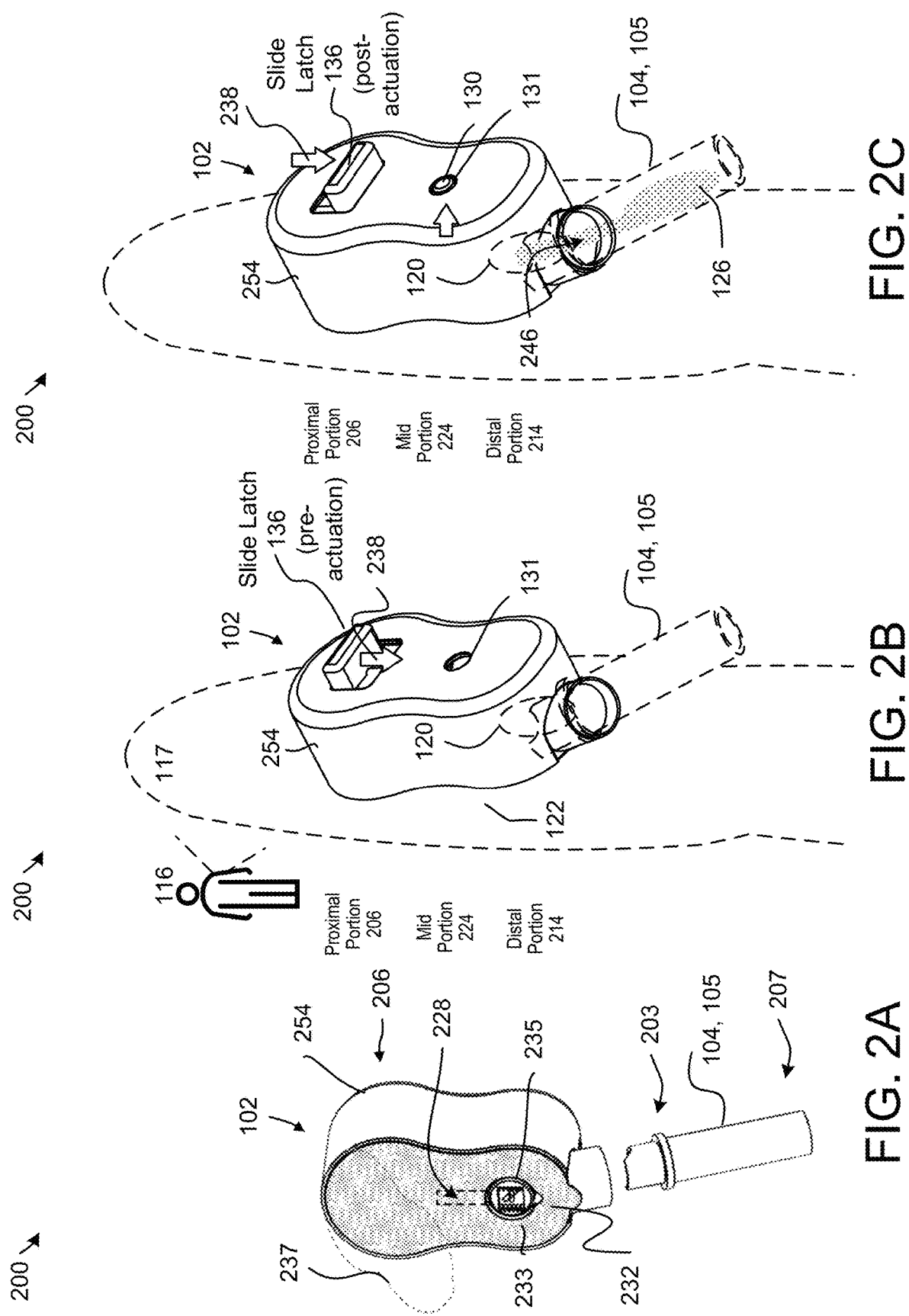

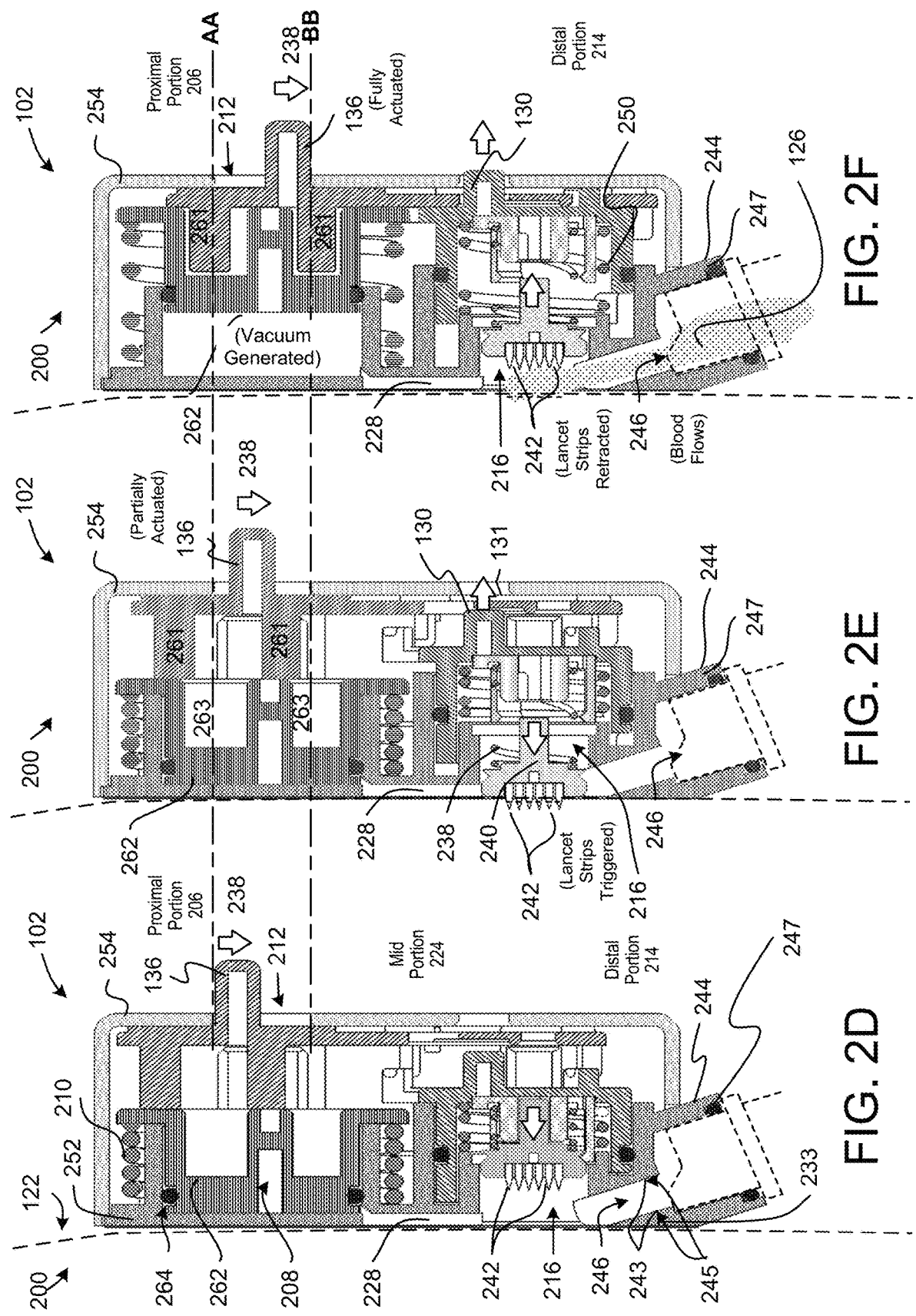

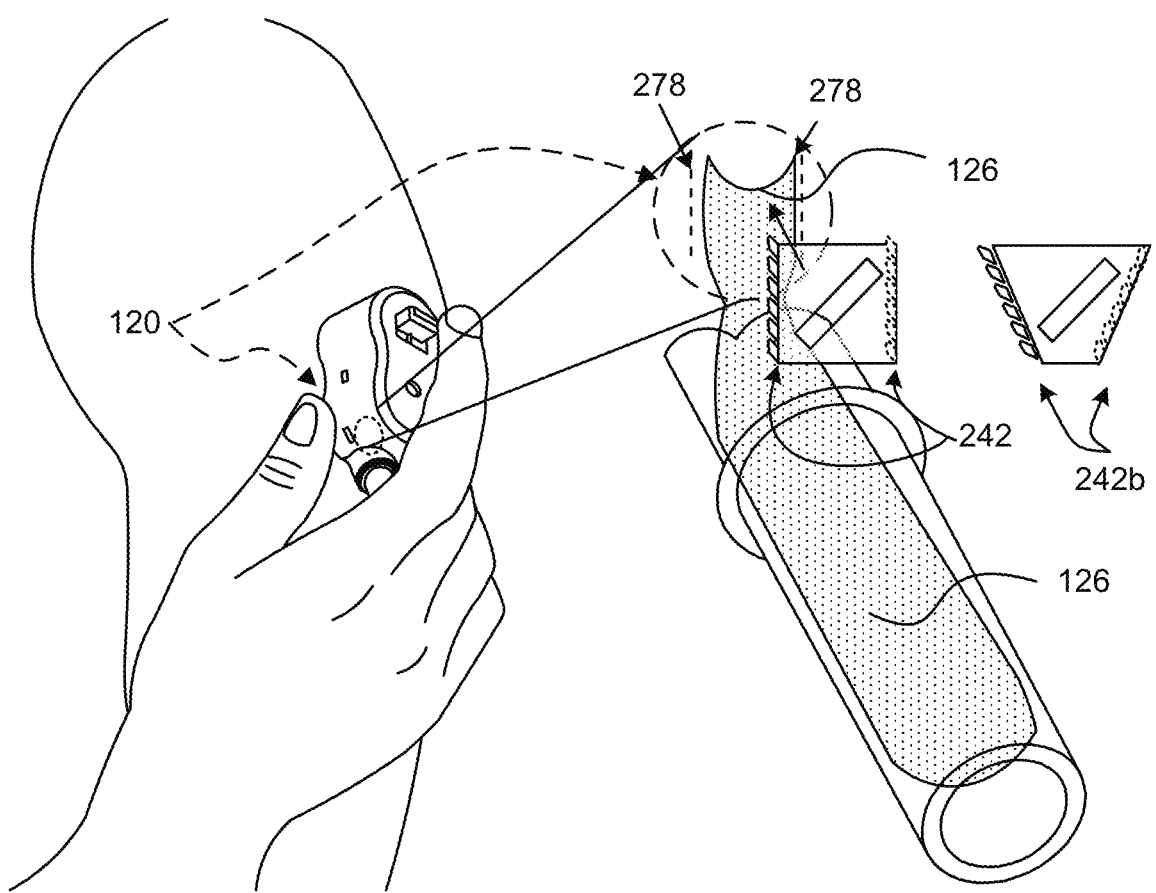
FIG. 2I
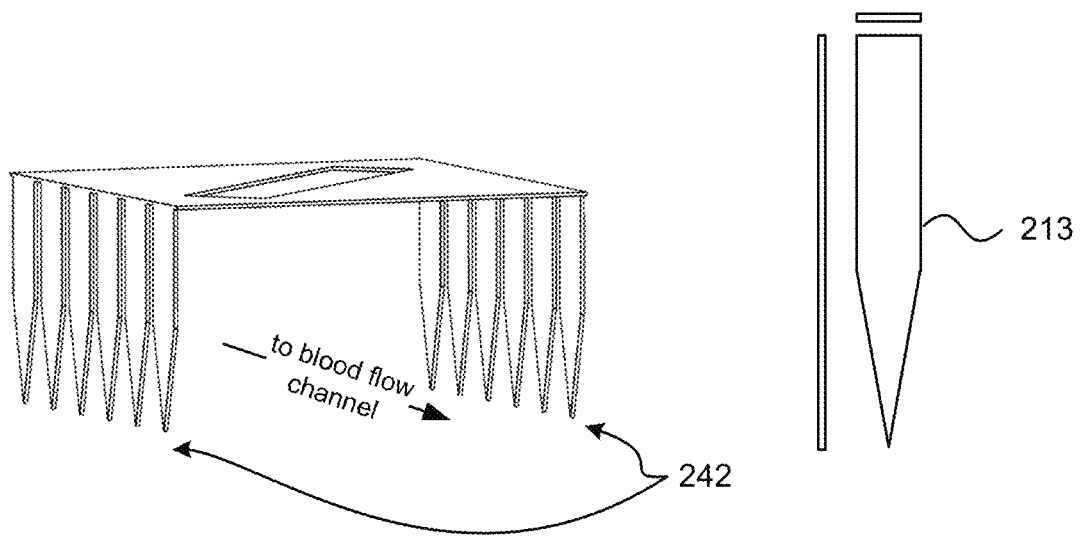
FIG. 2J
FIG. 2K

ACCELERATED ERGONOMIC COLLECTION OF CAPILLARY BLOOD

CROSS-REFERENCES TO RELATED APPLICATIONS

The present application is a continuation of U.S. application Ser. No. 18/081,475 titled "Accelerated Ergonomic Collection Of Capillary Blood" and filed Dec. 14, 2022 which claims priority to U.S. Provisional Application 63/400,277 titled Modular Self-Collecting and Processing of Peripheral Blood" filed on Aug. 23, 2022 the entire contents of each of the foregoing is incorporated herein by reference for all purposes permitted under application patent law and rules.

FIELD

The subject matter disclosed herein relates generally to devices for blood sample collection and more particularly relates to apparatuses, systems, and methods for accelerated ergonomic collection of capillary blood.

BACKGROUND

In today's growing market for health and wellness, blood samples and their components have the capability of being used for diagnosis or research. Blood collection and processing can be accomplished by various conventional methods and apparatuses. However, while these methods and apparatus have been used for many years, substantial problems with respect to the planning, procedural efficiency, duration and desirable amounts, purity, blood cell viability or quantities of blood cells, and the like, remain unresolved. Others can require a separate process for testing which may introduce possibility for contamination or may require the use of trained medical professionals.

BRIEF SUMMARY

A system and an apparatus for accelerated ergonomic collection of capillary blood are disclosed, the system and apparatus include a blood collection module including: a proximal portion including a vacuum generation chamber formed in a base, a vacuum piston, a precompressed volume expansion spring, and an enclosure with slot for a slide latch; a distal portion including a blood collection chamber formed in the base and configured to collect blood from a collection site in skin of a subject; a concave mid portion formed in the enclosure between the proximal portion and the distal portion of the enclosure to facilitate secure holding of the blood collection module between two digits of a hand, the concave mid portion further including a pressure equalization channel formed in the base and configured to equalize reduced air pressure within the vacuum generation chamber, the blood collection chamber, and within a transfer module coupled to the blood collection module.

The blood collection module also includes: a sealing surface at a bottom portion of the blood collection module and is configured to stably seal the blood collection module to the skin around the collection site; a slide latch configured to be actuated by a lengthwise sliding motion of a single digit of the hand relative to the blood collection module; a lancet carrier disposed within the distal portion and including a plurality of linearly-arranged lancet strips wherein, in response to the lengthwise sliding motion of the slide latch, the lancet carrier fires the plurality of linearly-arranged lancet strips to momentarily puncture and retract from a plurality of rows of blood extraction slits in the collection site; and an angled transfer port disposed at the distal portion of the blood collection module and configured to allow the blood to flow from the collection site through a low-resistance non-microfluidic blood flow channel to the transfer module, the angled transfer port extending outward from the blood collection module and being angled away from the subject at an acute angle of between 10 and 45 degrees relative to the sealing surface, wherein, in response to the plurality of rows of blood extraction slits being produced, blood components are guided to flow from an opening in the sealing surface through the low-resistance non-microfluidic blood flow channel to the transfer module via the angled transfer port.

The system further includes a plasma separation module configured to: receive collected blood from the transfer module decoupled from the blood collection module; and separate cellular blood components from blood plasma.

One or more methods are disclosed for accelerated ergonomic collection of capillary blood using the structures and/or functions of the disclosed systems and apparatuses.

BRIEF DESCRIPTION OF THE DRAWINGS

A more particular description of the examples briefly described above will be rendered by reference to specific implementations that are illustrated in the appended drawings. Understanding that these drawings depict only some examples and are not therefore to be considered to be limiting of scope, the examples will be described and explained with additional specificity and detail through the use of the accompanying drawings, in which:

FIG. 2A is an isometric bottom view of an apparatus including a blood collection module with skin adhesive for accelerated ergonomic collection of capillary blood according to one or more examples of the disclosure;

FIG. 2B is an isometric top view of an apparatus including a blood collection module shown before slide latch actuation for accelerated ergonomic collection of capillary blood, according to one or more examples of the disclosure;

FIG. 2C is an isometric top view of an apparatus including a blood collection module shown after slide latch actuation for accelerated ergonomic collection of capillary blood, according to one or more examples of the disclosure;

FIG. 2D is a sectional view of an apparatus including a blood collection module for accelerated ergonomic collection of capillary blood before slide latch actuation according to one or more examples of the disclosure;

FIG. 2E is a sectional view of an apparatus including a blood collection module for accelerated ergonomic collection of capillary blood after partial slide latch actuation according to one or more examples of the disclosure;

FIG. 2F is an isometric bottom view of an apparatus including a blood collection module for accelerated ergonomic collection of capillary blood after full slide latch actuation according to one or more examples of the disclosure;

FIG. 2I is a schematic diagram of an apparatus including a blood collection module with a magnified inset view of linearly-arranged lancet strips and an angled transfer module being used for accelerated ergonomic self-collection of capillary blood, according to one or more examples of the disclosure;

FIG. 2J is an isometric view of a plurality of linearly-arranged lancet strips configured to allow blood to flow from a plurality of rows of blood extraction slits through one or more channels between the linearly-arranged lancet strips, according to one or more examples of the disclosure;

FIG. 2K is an illustration of a top view, side view, and front view, of a lancet, such as used in the plurality of linearly-arranged lancet strips.

DETAILED DESCRIPTION

Figure 1:
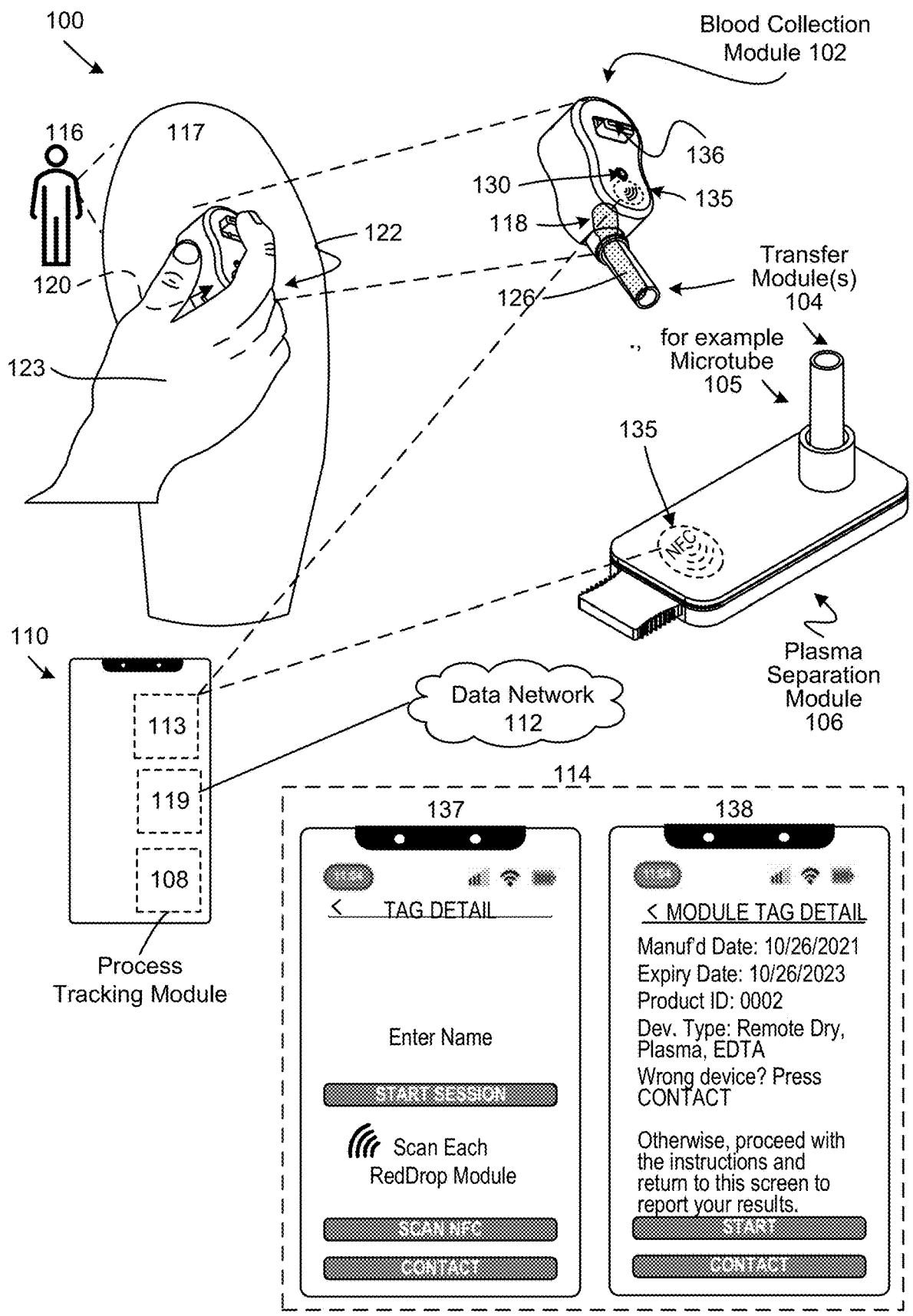
FIG. 1 is a schematic block diagram illustrating an overview of a system efficient and easy-to-use self-collecting and processing of capillary blood, according to one or more examples of the disclosure.

As will be appreciated by one skilled in the art, aspects of the examples may be implemented as a system, apparatus, and or method.

Furthermore, the described features, structures, or characteristics of the embodiments may be combined in any suitable manner. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

As will be appreciated by one skilled in the art, aspects of the disclosure may be implemented as a system, apparatus, method, or program product. Accordingly, aspects or implementations may take the form of an entirely hardware implementation, an entirely software implementation (including firmware, resident software, micro-code, etc.) or an implementation combining software and hardware aspects that may all generally be referred to herein as a "module," "controller," or "system." Furthermore, aspects of the disclosed subject matter may take the form of a program product implemented in one or more computer readable storage devices storing machine-readable code, computer readable code, and/or program code, referred hereafter as code. The storage devices may be tangible, non-transitory, and/or non-transmission. The storage devices may not embody signals. In a certain implementation, the storage devices only employ signals for accessing code.

Various of the functional units described in this specification have been labeled as modules or controllers. Certain of the modules described in the specification are primarily mechanical and/or fluidic modules. Some functions of a module or a controller may be implemented as a hardware circuit comprising semiconductors such as logic chips, transistors, or other discrete components, conductors.

For example, one or more modules may include an NFC tag used to convey information about a blood collection module, a transfer module. A module or controller may also be implemented in programmable hardware devices such as field-programmable gate arrays, programmable array logic, programmable logic devices or the like.

Certain types of modules or controllers may also be implemented in part or in whole, in code and/or software for execution by various types of processors. An identified controller or module of code may, for instance, comprise one or more physical or logical blocks of executable code which may, for instance, be organized as an object, procedure, or function. Nevertheless, the executables of an identified controller or module need not be physically located together but may comprise disparate instructions stored in different locations which, when joined logically together, comprise the module and achieve the stated purpose for the controller or module.

Indeed, a controller or a module of code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different computer readable storage devices. Where a controller, module or portions thereof are implemented in software, the software portions are stored on one or more computer readable storage devices.

Any combination of one or more computer readable medium may be utilized. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, measurement apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, measurement apparatus, or device.

Code for carrying out operations for some implementations may be written in any combination of one or more programming languages including an object-oriented programming language such as Python, Ruby, Java, Smalltalk, C++, or the like, and conventional procedural programming languages, such as the "C" programming language, or the like, and/or machine languages such as assembly languages. The code may execute entirely on the subject's computer, partly on the subject's computer, as a stand-alone software package, partly on the subject's computer and partly on a remote computer or entirely on the remote computer or server. In the latter scenario, the remote computer may be connected to the subject's computer through any type of network, including a local area network (LAN) or a wide area network (WAN), or the connection may be made to an external computer (for example, through the Internet using an Internet Service Provider).

Reference throughout this specification to "one example," "one implementation," "an example," "an implementation," or similar language means that a particular feature, structure, or characteristic described in connection with the example is included in at least one example. Thus, appearances of the phrases "in one example," "in an example," "in an implementation," and similar language throughout this specification may, but do not necessarily, all refer to the same example or implementation, but mean "one or more but not all examples" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

As used herein, a list with a conjunction of "and/or" includes any single item in the list or a combination of items in the list. For example, a list of A, B and/or C includes only A, only B, only C, a combination of A and B, a combination of B and C, a combination of A and C or a combination of A, B and C. As used herein, a list using the terminology "one or more of" includes any single item in the list or a combination of items in the list. For example, one or more of A, B and C includes only A, only B, only C, a combination of A and B, a combination of B and C, a combination of A and C or a combination of A, B and C. As used herein, a list using the terminology "one of" includes one and only one of any single item in the list. For example, "one of A, B and C" includes only A, only B or only C and excludes combinations of A, B and C. As used herein, "a member selected from the group consisting of A, B, and C," includes one and only one of A, B, or C, and excludes combinations of A, B, and C. As used herein, "a member selected from the group consisting of A, B, and C and combinations thereof" includes only A, only B, only C, a combination of A and B, a combination of B and C, a combination of A and C or a combination of A, B and C.

Also, as used herein, the term "about" generally means within 10%, 5%, 1%, or 0.5% of a given value or range.

Aspects of the examples and/or implementations are described below with reference to schematic flowchart diagrams and/or schematic block diagrams of methods, apparatuses, systems, and program products according to various example implementations.

The flowchart diagrams and/or block diagrams in the Figures illustrate the architecture, functionality, and operation of possible implementations of an apparatuses, systems, methods, and program products according to various examples and implementations. In this regard, each block in the flowchart diagrams and/or block diagrams may represent a module, segment, or portion of code, which includes one or more executable instructions of the code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted example. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and code.

The description of elements in each figure may refer to elements of proceeding figures. Unless otherwise clear from context, like numbers refer to like elements in all figures, including alternate implementations of like elements.

Introduction and Overview

Generally, the present disclosure describes systems, methods, and apparatus for self-collecting and processing capillary blood. More specifically, the present disclosure relates to systems and methods for gathering a blood sample, in a closed disposable module, and a method to package that blood or its components in wet or dry forms in another device or container for further processing such as testing, storage, transportation, or use in medical diagnostic, treatment or research applications. Further the disclosure provides ways to track the location of the device and to share device data with data networks and other devices.

The inventors of the subject matter of the present disclosure have identified a need for a cost-effective and simple blood collection device which is optimized to be self-operated by a person who needs to draw a small amount of blood for the purposes of using that blood to make a wellness, fitness, or medical determination of the person's health.

Capillary blood can be useful for a variety of laboratory tests such as a basic metabolic panel, bilirubin, blood urea nitrogen/creatinine ratio, complete blood count (CBC), comprehensive metabolic panel, cortisol, ferritin, glucose, immunoglobulins tests, liver function tests, osmolality, thyroid function test, triglycerides, to name just a few.

Without the system, apparatus, and methods disclosed herein, existing methods may have numerous drawbacks even for relatively small amounts of blood. Some direct-to-consumer kits provide lancets and microtubes, or lancets integrated with a microcontainer for performing finger prick blood collection.

Moreover, using the finger prick method, only a limited amount of blood can be drawn. The pads of fingertips have a high density of nerve endings and finger pricks can be painful even when pricking the sides. Squeezing a finger too tightly can dilute the specimen with tissue fluid (plasma) and increases the probability of damage to the blood cells (hemolysis). Scarring may occur when there have been multiple punctures in the same area.

If a capillary blood collection device collects only a limited volume of blood (e.g., less than one hundred μL), there may be insufficient volume of blood to conduct the needed tests and doing more than one draw with the same device may increase the risk of infection, leakage, pain, etc.

Stability during operation may be an issue if the height of a blood collection device is as large or is larger than the width of the device at the base. Such devices may be more easily tipped or unintentionally dislodged creating a risk of leakage and/or possible contamination. Furthermore, it may be challenging for a subject who is collecting blood from himself or herself to directly see a fill level of a connected microtube if a connected collection container such as a microtube is not angled away from the skin of the subject but is instead generally parallel to the base of the blood collection device.

In various blood collection sample circumstances, considerations such as anxiety related to seeing blood being collected from one's forearm or where concerns about potential temporary wounds being more visible on an anterior forearm, the apparatuses and methods disclosed herein may be used for blood collection on a shoulder, upper arm, or other body areas. For example, for small children such other body areas may include a lower back region, or for animals, other body areas may include vertical regions of skin which are shaved or otherwise hairless may be used as suitable collection sites.

The inventors of the subject matter of the present disclosure have identified a need for a cost-effective and simple blood collection device which is optimized to be self-operated by a person who needs to draw a small amount of blood for the purposes of using that blood to make a wellness, fitness, or medical determination of the person's health.

FIG. 1 is a schematic block diagram illustrating an overview of a system 100 for accelerated ergonomic collection of capillary blood, according to one or more examples of the disclosure.

As noted above, although capillary blood sampling has been used to collect very small amounts e.g., ten to twenty microliters of blood from a small puncture/prick in a finger, heel, earlobe, big toe, or palm, various problems such as formation of calluses, low volume of blood collected, slow blood flow, and/or cumulative pain with repeated pricking.

Some capillary blood collection systems have used microneedles or microfluidics in an attempt to reduce the pain associated with finger pricks and to try to collect larger volumes of blood. However, certain systems have low-volume or slow blood flow due to the small size of the microneedles and/or microfluidic blood flow channels which may lead to incomplete blood collection or may cause hemolysis, which is the rupture, destruction, or breakdown of red blood cells which can have an effect on laboratory results. For example, certain blood samples containing more than one hundred mg/dL of hemoglobin can cause nonspecific binding in serological tests.

Accordingly, the inventors of the subject matter disclosed herein have applied ergonomics, which is an applied science concerned with designing and arranging things people use so that the people and things interact most efficiently and safely to develop an accelerated ergonomic capillary blood collection system designed to be rapidly, safely, and easily self-operated by a subject. In certain circumstances, such as with infants, animals, and other subjects with limited physical or mental capacity, the system 100 may be operated by another person such as a healthcare professional.

The amount of blood collected using the system 100 is designed to be of a sufficient volume and quality that the blood is useful for a medical determination such as a diagnostic test. The system 100 includes three types of modules. A first type of module is a blood collection module 102. The blood collection module 102 is designed to be mechanically and adhesively coupled to a collection site of skin 122 on a body part 117 of the subject. In various examples, the blood collection module 102 includes an angled transfer port (244 that allows a transfer module 104 to be coupled an angle so that it is readily visible while gravity-assisted transfer of blood from the blood collection module 102 to the transfer module 104 is performed.

The transfer module 104 enables blood to be immediately removed from the device for immediate testing, or to be transferred to a storage location, or to a laboratory testing location. In various example implementations, certain blood components such as DNA, red blood cells, white blood cells, proteins, etc. are kept intact for further processing. It may be noted that as used herein, descriptions of blood components flowing are understood to refer to blood and its components flowing, unless otherwise clear from context. For example, In certain example implementations, the blood collection and dispensing components are designed for single use and may be discarded and disposed of in a clean way, especially if done at home or in a non-medical facility. Beneficially, the system 100 enables a subject to electronically receive and/or share data related to the blood collection module 102 or the transfer modules 104 with laboratories and providers, for purposes of location tracking, safety, or device data sharing.

The system 100 may include various types of transfer modules 104, such as for example a microtube 105, a plasma separation module 106, a dried blood module (not shown), a dried plasma module (not shown), and/or a reagent adder module (not shown). Further details regarding the blood collection module 102, the transfer modules 104, and the process tracking module 108 are provided below.

In certain implementations, the system 100 includes a transfer module 104 with a transfer opening at proximal end with an inner diameter of about 10 mm and an outer diameter of about 13 mm. In some examples, the transfer module includes a prepackaged additive selected to mix with the capillary blood to facilitate performance of one or more predetermined laboratory tests.

Figure 6:
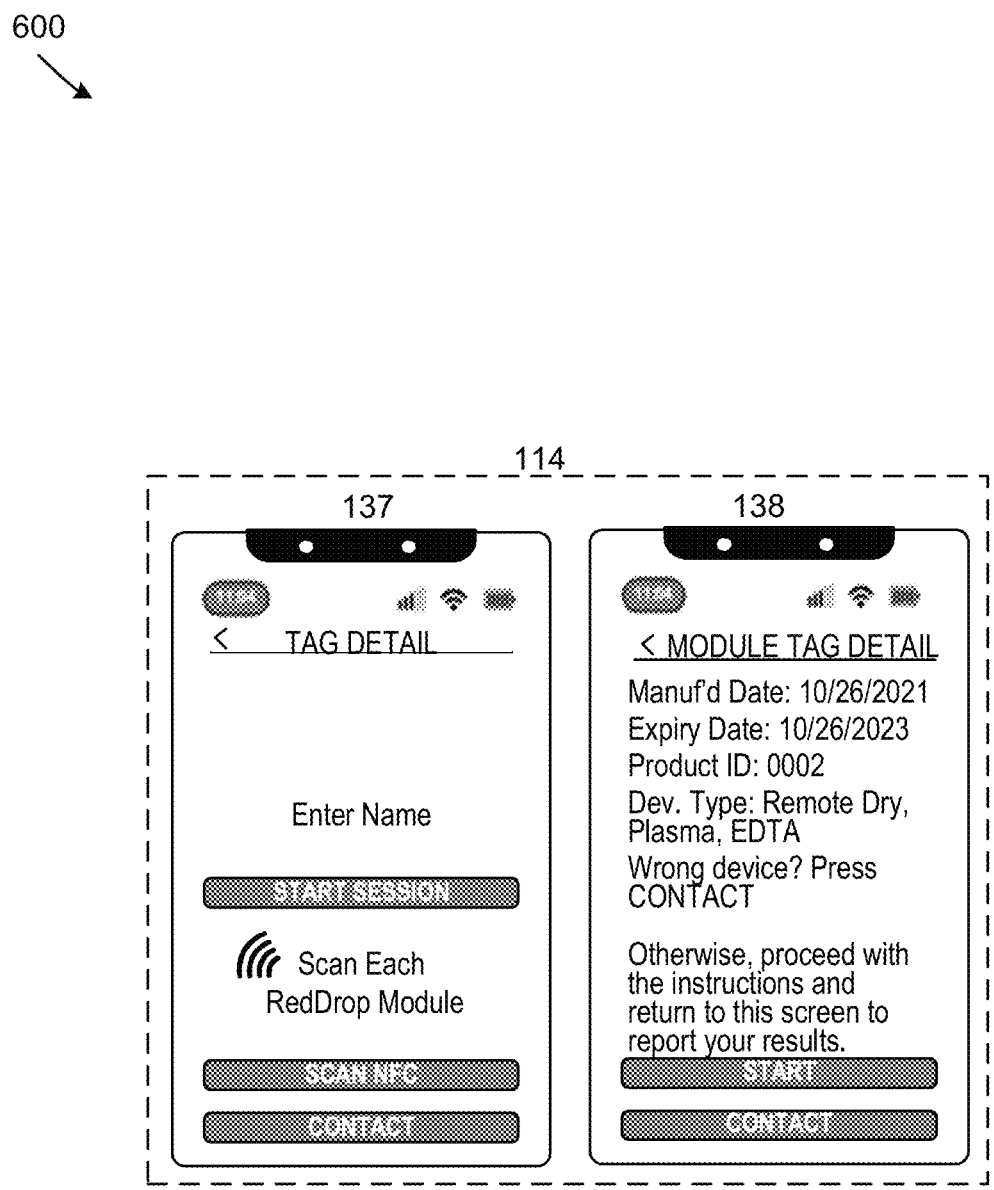
FIG. 6 is an illustration of onscreen communications related to confirming proper use of the system for accelerated ergonomic collection of capillary blood, according to one or more examples of the disclosure.

In various implementations, the system 100 includes a process tracking module 108 that is configured to provide information about how to perform a predetermined blood collection process using a transfer module 104 e.g., a microtube 105, with the blood collection module 102 according to instructions determined by a healthcare provider, a requesting laboratory, an agency, an employer, or other entity involved with the selected blood testing. For example, as depicted in FIG. 6, a subject may be instructed via an onscreen communication 137 on a display of a portable electronic device 110 such as a smart phone, to enter their name and to perform an NFC scan of each module that they intend to use. The term "NFC" refers to near-field communication which is a set of communication protocols that enables communication between two electronic devices such as the NFC scanner 113 and an NFC tag 135 over a short distance. This can be done by starting the application that implements the process tracking module 108, entering the subject's name, and following the displayed instructions to scan each module using the NFC scanner 113 e.g., by touching the scan NFC icon on the application display.

When the NFC scan is completed, an onscreen communication 138 may show module information based on data bits stored in the NFC tag 135 which may also be used as an index to additional information which may be accessed through a data network 112. As depicted in the onscreen communications 137, 138, a subject may be asked to enter their name, scan modules, and confirm that information displayed electronically in response to the NFC tag scan matches written or electronic information conveyed to a subject by mail or email.

Further details about the process tracking module 108 and various content or communications that may be displayed on the portable electronic device 110 are provided below in the detailed description of FIGS. 5, 6, and 7.

FIGS. 2A-2I. The following disclosure includes a number of different figures related primarily to the blood collection module 102, components that may be included in the blood collection module 102, internal structures, mechanisms, and functions relating to the blood collection module 102, use cases for the blood collections module 102, and so forth.

Figure 2G:
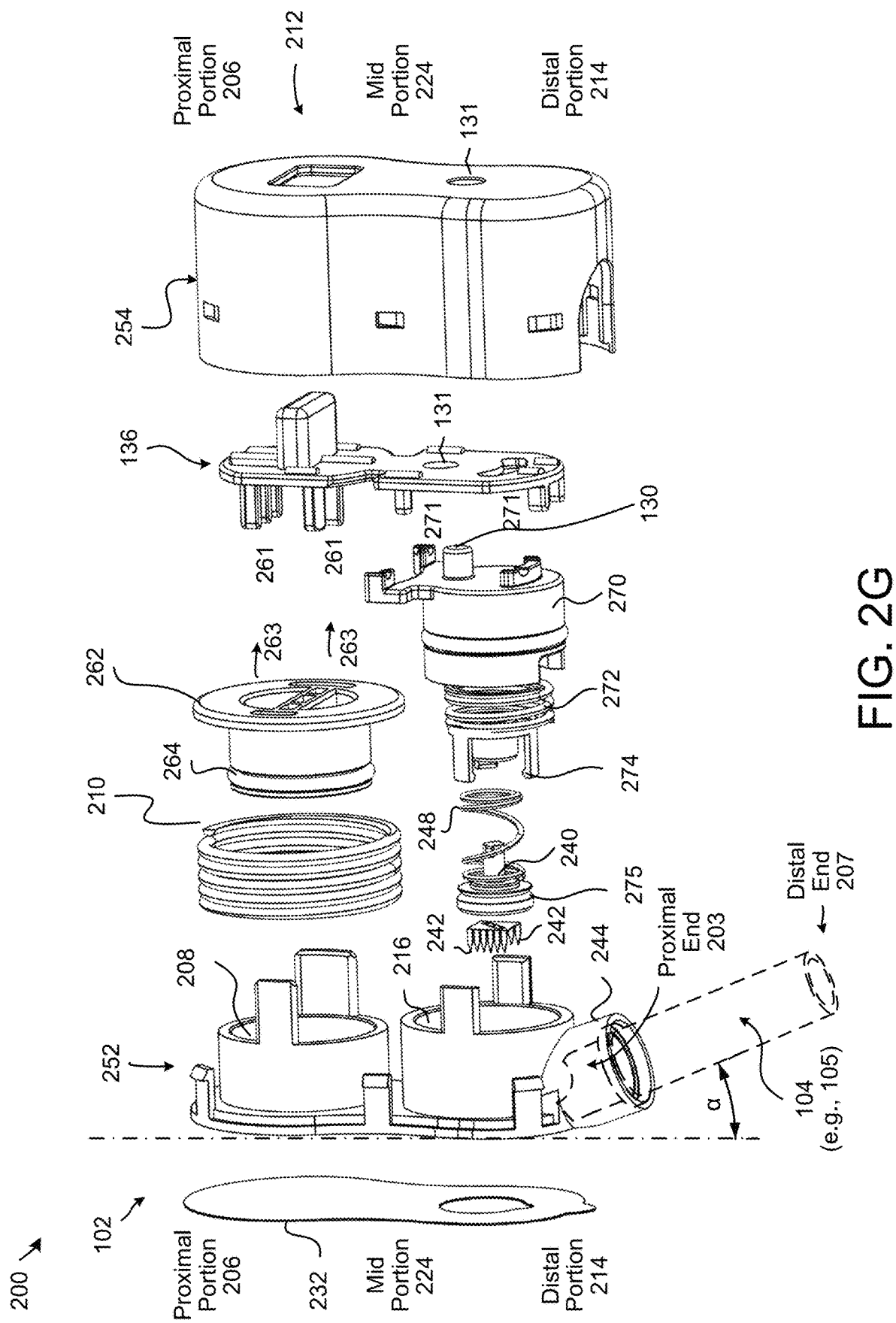
FIG. 2G is an exploded isometric side-top view of an apparatus including a blood collection module for accelerated ergonomic collection of capillary blood after slide actuation according to one or more examples of the disclosure.
Figure 2H:
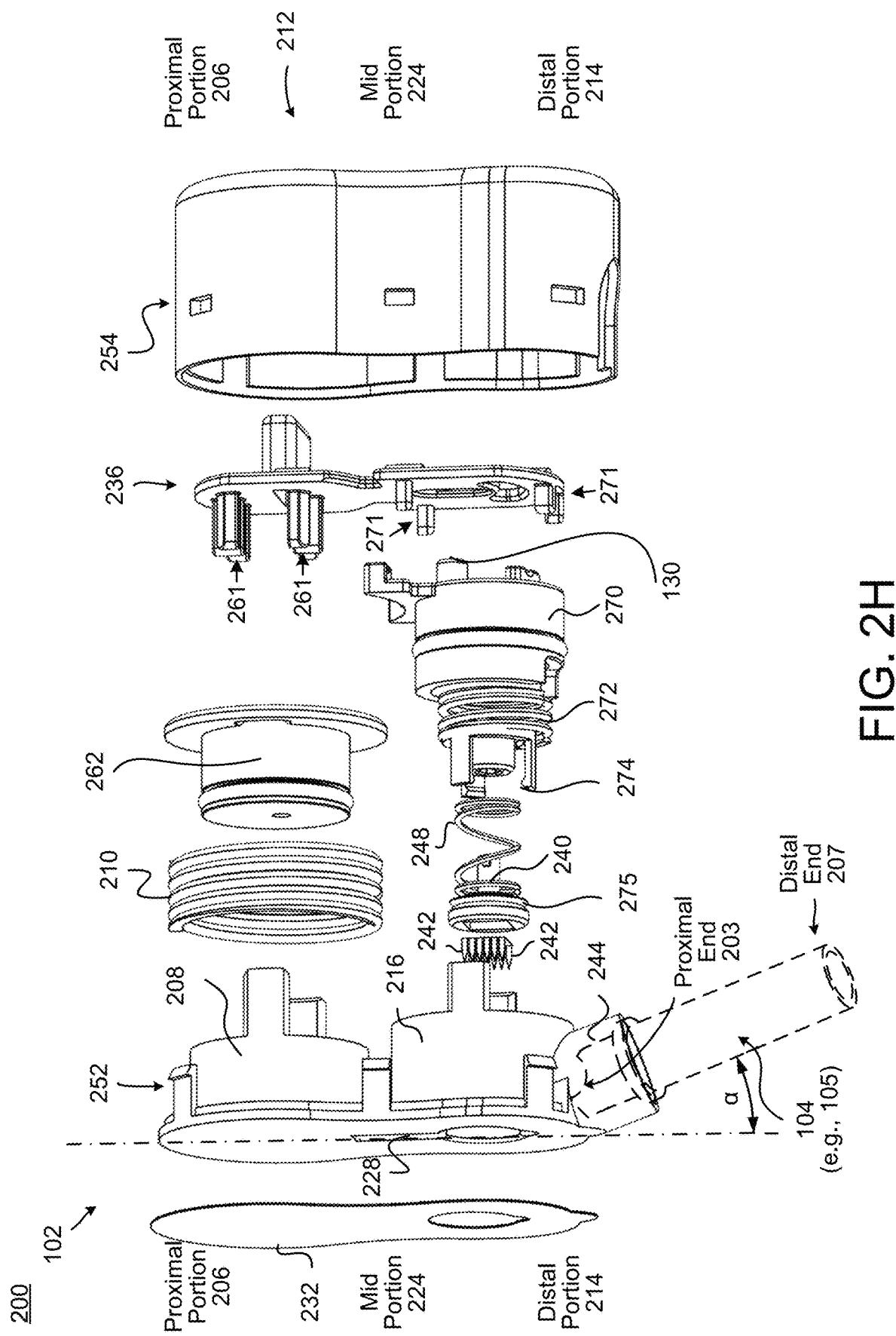
FIG. 2H is an exploded isometric side-bottom view of an apparatus including a blood collection module for accelerated ergonomic collection of capillary blood after slide actuation according to one or more examples of the disclosure.

FIGS. 2A-2C illustrate and describe the high level structures and functions of the blood collection module 102 as experienced by the subject 116 or a user if someone other than the subject 116 actuates the blood collection module 102. FIGS. 2D-2F illustrate, describe the inner components, and functions the blood collection module 102 using a cross-sectional perspective. FIGS. 2G-2H illustrate and describe details related to the blood flow speed and efficiency of blood from multiple rows of blood extraction slits created by multiple linearly-arranged lancet strips 242 through the non-microfluidic channel in the transfer port to the transfer module 104.

FIG. 2A is an isometric bottom view of an apparatus 200 including a blood collection module 102 with a skin adhesive 233 to facilitate accelerated ergonomic collection of capillary blood according to one or more examples of the disclosure.

In the selection and ergonomically beneficial skin adhesive 233 for a blood collection module 102, it is important to take into account various trade-offs relating to a weight bearing adhesive that will hold the blood collection module 102 on a body part 117 of the subject 116 for the short time it takes to collect the blood 126 and at the same time will avoid excessive skin irritation and discomfort to the subject even when used frequently for the same region of skin 122. Different types of adhesives may be used for different types of subjects. Thus, safe and ergonomic removal of the blood collection module 102 is also an important factor. For example, different skin adhesives may be used for persons with skin sensitivity, infants, various types of animals, or other subjects with special requirements.

In various implementations, the skin adhesive 233 comprises a double-sided elastic adhesive film or adhesive tape that aggressively attaches to the sealing surface 232 at a subject facing portion of a base 252 and securely but gently adheres temporarily to the skin 122 of the subject 116.

In certain examples, the skin adhesive 233 in tape or film form may include one or more of synthetic rubber, acrylic silicone, hydrocolloid, and/or combinations thereof. In some examples, the skin adhesive in tape or film form has sufficient thickness and elasticity to elastically seal the blood collection module 102 to the skin 122 of the subject 116 with sufficient sealing quality even with subjects where there may be a few hairs or other nonuniformities in the skin 122 of the subject 116. Various examples of suitable skin adhesive 233 in tape or film form may be obtained from Vancive Medical Technologies of Chicago, Illinois, USA, or 3M Company of St. Paul, Minnesota, USA and other sources that may be known to skilled persons in the field.

In one or more examples, the blood collection module 102 is shipped with a release liner 237 which may be removed just prior to adhesively coupling the blood collection module 102 to the region of skin 122 of the subject. The skin adhesive 233 facilitates sealing the sealing surface 232 of the base 252 (depicted in FIGS. 2D-2F) so that a partial vacuum can be formed above the collection site 120 to facilitate accelerated ergonomic blood collection.

As depicted in FIG. 2A, the skin adhesive 233 in film or tape form also serves as a subject facing wall of a pressure equalization channel 228 formed in a base 252 where the pressure equalization channel 228 facilitates creation of a partial vacuum at an opening 235 in a distal portion of the base 252 (as further depicted and described with respect to FIG. 2G). With the blood collection module 102 position on the skin 122 of the subject 116 such that the proximal portion 206 is higher than the distal portion 214, accelerated blood flow is enhanced as shown in FIG. 2C. This improvement is further depicted a in the onscreen communication 710 shown in FIG. 7.

Another ergonomic improvement of the disclosed angled transfer port 244 is that it facilitates decoupling of the blood collection module 102 with less mess. In certain implementations, with the transfer module 104 being coupled to the blood collection module 102 and disposed perpendicularly to a support surface, the angled transfer port 244 causes the opening 235 in the sealing surface 232 of the blood collection module 102 to face at least partially upward to inhibit blood residue from spilling from the opening 235 during decoupling of the transfer module from the angled transfer port 244.

When blood collection is completed, the transfer module 104 may be rested perpendicularly to a surface such as a table or a desk and the blood collection module 102 may be twisted off in such a way that spillage from the opening 235 does not occur because holding the transfer module 104 perpendicular to the surface causes the opening to be at least partially angled upwards thus inhibiting spillage.

FIGS. 2B-2H provide further details regarding the structures and functions related to the blood collection module 102.

FIG. 2B is an isometric top view of an apparatus 200 including a blood collection module 102 shown before slide actuation for accelerated ergonomic collection of capillary blood. In many implementations, the slide latch 136 of the blood collection module 102 is configured to be easily actuated by a subject who is doing self-collection of blood, such as for example, when requested by a physician, employer, or other entity, so that one or more laboratory tests may be performed on a blood sample from the subject.

One of the various ergonomically beneficial aspects of the slide latch 136 of the blood collection module 102 is that because there is no significant counterforce pushing back against a user's finger or hand in a direction opposite the direction of actuation, actuation of the blood collection module 102 is significantly easier than existing devices as will be explained in more detail below.

Another ergonomic aspect is that there is an actuation indicator opening 131 through which a user can see or feel whether the blood collection module 102 has been actuated. In existing devices, the amount of force needed to perform actuation is significant and the pressure or pain may be significant enough that the user may find it hard to tell the blood collection device has been actuated. Further details are provided below about how the blood collection module 102 solves such problems found in existing devices.

As further depicted in FIG. 2B, with the slide latch 136 in a pre-actuation condition, the user can see a portion of the slide latch 136 through the actuation indicator opening 131. In various implementations, the color of the protruding portion of the slide latch 136 which is moved by the user using a lengthwise sliding motion 238 is the same color as a portion of the slide latch that can be seen through the actuation indicator opening 131. Prior to actuating the slide latch, a transfer module 104, such as for example, a micro tube 105 is coupled to the blood collection module 102 in a way that facilitates ergonomic coupling, viewing, and decoupling of the transfer module throughout the collection of capillary blood.

FIG. 2C is an isometric top view of an apparatus 200 including a blood collection module 102 shown after slide actuation for accelerated ergonomic collection of capillary blood. As noted above with respect to FIGS. 1, 2B, in some implementations, the blood collection module 102 includes a slide latch 136 that is configured to be ergonomically actuated by a lengthwise sliding motion 238 of a single digit (e.g., index finger) of the hand 123 relative to the blood collection module 102.

Various ergonomic aspects of the blood collection module 102 are further enhanced by the accelerated blood flow facilitated by the structures and functions disclosed herein. In some existing systems, a user or a subject may need push down on an actuator for several seconds or more and may further need to wait as much as one minute before being able to tell whether they device has been properly actuated and blood is beginning to be collected. However, as described in more detail below, a user using the blood collection module 102 can determine immediately that the blood collection module 102 has been actuated by viewing or feeling the position of the slide latch 136 and by viewing or touching the actuation indicator 130, which may have a different color than the slide latch and may be felt and seen protruding from the actuator indicator opening.

Furthermore, in various implementations because the blood collection module 102 includes a blood flow channel 246 that is at least 30% as large as the minimum inner cross-sectional area of the transfer module 104 through which blood 126 collected using the blood collection module 102 is configured to flow, accelerated ergonomic collection of capillary blood is facilitated.

FIG. 2D is a sectional view of an apparatus 200 including a blood collection module 102 for accelerated ergonomic collection of capillary blood before slide latch actuation. Distinct from some existing blood collection devices in which create a reduced pressure volume through which the actuator and one or more needles move, the blood collection module 102 disclosed herein ergonomically separates the vacuum generation structures and functions, which are generally disposed in a proximal portion 206 of the blood collection module 102 from the blood extraction structures and functions including the lancet strips, which are generally disposed in a distal position 214 of the blood collection module 102. The actuation structures and functions including slide latch 136 are generally separate from but spanning across both the vacuum generation structures and functions in the proximal portion and the blood extraction structures and functions in the distal portion 214.

Furthermore, the ergonomic shape of the enclosure 254 of the blood collection module 102 it is enhanced by a concave midportion 224, making it easier to position on the skin, easier to remove, easier to actuate, and giving it an overall much lower profile than existing devices in which vacuum generation structures and functions, blood extraction structures and functions, and actuation structures and functions, generally occupy the same space or significantly overlapping spaces, FIG. 2E is a sectional view of apparatus 200 including a blood collection module 102 for accelerated ergonomic collection of capillary blood after partial slide latch actuation. Various accelerated ergonomic capillary blood collection functions are configured to be performed based on the unique structure of the slide latch 136 interacting across both vacuum generation structures and functions as well as blood extraction structures and functions. For example, one notable improvement over existing devices is that even when using the same base 252 and enclosure 254, the timing of the vacuum generation and the triggering of the lancet strips is mechanically selectable by a configuring the blood collection module 102 with a slide latch 136 that has different positioning of the vacuum piston blocking elements 261 and the extraction collar blocking elements 271 which are shown and described in more detail with respect to FIGS. 2G and 2H.

FIG. 2F is an isometric bottom view of an apparatus 200 including a blood collection module 102 for accelerated ergonomic collection of capillary blood after fully actuating the slide latch 136. As noted above, the relative positioning of the slide latch 136 to the vacuum generation structures in the proximal portion 206 and the blood extraction structures is the distal portion 214 is depicted for a circumstance in which it is preferable to puncture blood extraction slits as depicted in FIG. 2E with earlier timing selected then the timing selected for generating a vacuum in the vacuum chamber 262. However, not only can the order of the skin puncturing and vacuum generation functions depicted as shown, reversed, or configured to occur at the same time, but even within a particular order the timing of each function is configurable based on positioning of the different blocking elements 261, 271 which are depicted and described in more detail with respect to FIGS. 2G and 2H.

FIG. 2G is an exploded isometric side-top view of an apparatus 200 including a blood collection module 102 for accelerated ergonomic collection of capillary blood. This exploded top view highlights the ergonomic and efficient design of the blood collection module 102. Three different springs are provided including a volume expansion spring 210, a collar spring 272, and a lancet carrier spring 248 are shipped in a precompressed state. Together, and individually, these springs represent a significant ergonomic improvement over existing devices where a spring or a springy elastomeric member must be pressed upon or otherwise have a counter force applied to it to operate such devices.

The exploded top view of FIG. 2G highlights that in various implementations, the blood collection module 102 may be manufactured using a relatively small number of molded biocompatible components. Additionally, the exploded top view provides a three-dimensional perspective of the carrier latch 274 utilized in the depicted implementation which retains the multiple lancet strips 242 from being fired into the skin until the timing configured by the slide latch 136 being actuated by sliding causes the precompressed lancet carrier spring 248 to propel the lancet strips 242 into the skin. In some implementations, the carrier latch 274 includes three spatially distributed prongs that assist in retaining the lancet carrier securely in place until the slide latch 136 is actuated. Further details about the depicted implementation are provided below.

FIG. 2H is an exploded isometric side-bottom view of an apparatus 200 including a blood collection module 102 for accelerated ergonomic collection of capillary blood. FIG. 2H is similar to FIG. 2G except that exploded slide-bottom view provides a three dimensional perspective highlighting one example implementation of the pressure equalization channel formed in the mid-portion 224 of the base 252.

Continuing with the detailed description of FIGS. 2A-2H, the use of the same or similar numbers referring to different components and subcomponents of the blood collection module 102 which are included in more than one of FIGS. 2A-2H should be understood to refer to the same structures and functions unless otherwise clear from context. FIGS. 2A-2H provide different types of detailed views of various example implementations of structures and functions that may be included in the blood collection module 102. Various elements or components of the blood collection module 102 are depicted using reference numbers in FIGS. 2A-2H that may be included in certain figures and may not be repeated in portions of the detailed description corresponding to the Figures in order to highlight different aspects of the blood collection module 102.

As can further be seen in FIGS. 1, 2B and 2C, in various implementations, the blood collection module 102 includes a concave mid portion 224 formed in the enclosure 254 between a proximal portion 206 and a distal portion 214 of the enclosure 254 to facilitate secure holding of the blood collection module 102 between two digits (e.g., thumb and middle finger) of a hand 123.

Implementation of these ergonomic structures and functions in the blood collection module 102 specifically improve the ease of operation, stability, and reliability of the disclosed blood flow collection module 102 relative to existing devices which exhibit many of the ease-of-use, reliability, and stability problems described above in the Introduction and Overview section that precedes the detailed description of FIG. 1.

Similarly, accelerating features including a low-resistance non-microfluidic blood flow channel 246 and an angled transfer port 244 disposed at the distal portion 214 of the blood collection module represent substantial improvements over existing technologies which exhibit various problems in slow blood flow rate, coagulation, and incomplete blood collection some of which are described above in the introduction and overview section that precedes the detailed description of FIG. 1.

In various examples, the blood collection module 102 includes a base 252, and enclosure 254, a slide latch 136, and a skin adhesive 233 for securing the base 252 to the skin 122 of the subject 116. Accordingly, the blood collection module 102, in various examples, includes a proximal portion 206 comprising a vacuum generation chamber 208 formed in the base 252, a vacuum piston 262, and a precompressed volume expansion spring 210, and a slide latch slot 212 formed in the enclosure 254.

In the pre-actuation state, the vacuum piston 262 is biased by the volume expansion spring 210 in a precompressed state and is retained in a pre-actuation/pre-vacuum generation position by a portion of the slide latch 136. The vacuum piston 262 includes an O-ring 264 that hermetically seals against the walls of the vacuum generation chamber 208 such that when the slide latch 136 is actuated by a lengthwise sliding motion 238, the precompressed volume expansion spring 210 is no longer retained and expands pushing a vacuum piston 262, away from the sealing surface 232 thereby generating a partial vacuum within the vacuum generation chamber 208.

More specifically, in an implementation depicted in FIGS. 2E, 2F and 2G, when one or more vacuum piston blocking members 261 are slid far enough distally toward the transfer module 104 that the vacuum piston cavities 263 can be pushed away from the sealing surface so that the vacuum piston blocking members 261 are positioned within the vacuum piston cavities 263, the precompressed volume expansion spring 210 expands away from the sealing surface 232 and at least a partial vacuum is generated by the effective expansion of volume sealed the vacuum generation chamber 208.

Similarly, a distal portion 214 of the slide latch 136 includes certain extraction collar blocking elements 271 that maintain the extraction collar 270 with the collar spring in the precompressed state. When the slide latch is slid lengthwise toward the transfer module 104, far enough that the extraction collar blocking elements 271 no longer press against the extraction collar 270, the extraction collar 270 will be pushed away from the sealing surface such that the carrier latches 274 are pulled away from the lancet carrier foot 275 which triggers the lancet carrier 240 to be propelled toward the sealing surface 232 such that the lancet strips 242 momentarily puncture the skin 122 of the subject 116 creating rows of blood extraction slits 278 in the skin 122 of the subject 116.

Furthermore, in response to the slide latch 136 being actuated by the lengthwise sliding motion 238, the actuation indicator 130 is configured to both visually and haptically indicate that the blood collection module 102 has been actuated. More specifically, in one or more implementations, the actuation indicator 130 is formed on the outward facing surface of the extraction collar 270 using material that has a different appearance e.g., different color such as red that becomes visible when the extraction collar 270 pushes outward extending the actuation indicator 130 through the actuation indicator openings 131 in the distal portion 214 of the slide latch 136 and the enclosure 254.

Accordingly, the visually different appearance of the actuation indicator 130 from the enclosure 254 can be seen when the slide latch 136 is in the fully actuated position depicted in FIGS. 1, 2C, and 2F. Likewise, because the actuation indicator 130 protrudes slightly above the outward surface of the enclosure 254 at the actuation indicator opening 131, a person can use the sense of touch to feel the protruding actuation indicator 130 thereby confirming that the slide latch 136 has been fully actuated.

This actuation indicator 130 is an ergonomic improvement over existing blood collection devices when used may create concern or confusion for a user because it is challenging to determine whether such existing blood collection devices have indeed been activated.

Furthermore, the disclosed approach to generating a vacuum solves several problems found in existing blood collection devices. One problem with vacuum-assisted blood collection is found in existing designs for blood collection devices which use a first approach for vacuum generation of incorporating into the blood collection device, a self-contained vacuum chamber, or a vacuum chamber having a volume that is at a pressure less than ambient pressure prior to actuation. However, to maintain a pressure less than ambient pressure prior to actuation for any substantial period of time suggests that such a pre-depressurized chamber should either be nearly leakproof or potentially risk failure upon actuation because the pressure differential between the vacuum chamber and ambient pressure is less than desired due to leakage over time.

Accordingly, in view of the challenges associated with maintaining less than ambient air pressure over time in a blood collection device vacuum chamber, a second approach taken in existing designs is to push, depress, or squeeze an elastomeric component such as a bulb, bellows, flexible concave membrane, or similar vacuum source that can be compressed by a user such that air is expelled and when the pushing or squeezing stops, a partial vacuum is generated by the return of the elastomeric component to its original shape. Unfortunately, this second approach may also present several problems.

For example, to evacuate air out of an elastomeric vacuum generating component by pushing, depressing, squeezing or the like, may require significant effort on the part of the person doing the pushing, depressing, squeezing, etc. Some subjects who need or want to have blood tested fairly regularly may lack the strength to push, depress, squeeze the elastomeric component (or similar) completely so that the level of air pressure reduction may be inconsistent from time to time which may result in incomplete blood collection e.g., less than the desired volume. Additionally, some existing devices use microfluidics, one-way valves, pressure regulators.

Furthermore, as noted in the earlier introduction section of this disclosure, applying a significant amount of downward mechanical pressure (i.e., toward the subject) to a "push-to-actuate" type of actuator in a blood collection device may cause the blood collection device to slip or wobble and may potentially break a seal formed between the bottom of the device and the subject's skin. This may be especially relevant to blood collection devices with a height that is greater than a base dimension. Moreover, many people who might use a blood collection device have to collect blood relatively frequently and having to apply pressure frequently for the purpose of generating a vacuum. Applying significant pressure towards a subject's body may cause pain, bruising, or other damage to the subject and experiencing these problems, especially on a frequent basis, may discourage people from using such blood collection devices.

In contrast to existing devices, the blood collection module 102 disclosed herein uses an ergonomic design which does not require maintaining lower than atmospheric pressure prior to actuation and does not require the slide latch 136 to be depressed, pushed, or compressed towards the subject's body to provide the energy to generate a vacuum. Instead, the energy used to generate the vacuum is stored in the precompressed volume expansion spring 210 and the slide latch 136 is merely actuated by a short, gently lengthwise sliding motion 238 toward the proximal end 203 of the transfer module 104 (e.g., microtube 105) which is coupled to an angled transfer port 244 formed in a distal portion 214 of the base 252.

The blood collection module 102, as illustrated in FIGS. 2B and 2C, further includes a concave mid portion 224 formed in the enclosure 254 between the proximal portion 206 and the distal portion 214 of the enclosure 254 to facilitate secure holding of the blood collection module 102 between two digits of a hand 123.

In various implementations, the concave mid portion 224 further includes a pressure equalization channel 228 formed in the base 252 and configured to equalize reduced air pressure within the vacuum generation chamber 208, the blood extraction chamber 216, and a transfer module 104 coupled to the blood collection module 102.

With respect to the proximal portion 206, the distal portion 214, and the concave mid portion 224, these references are intended to convey the relative location of various parts of the base 252 and the enclosure 254 and should not be interpreted as describing strict boundary lines that define each portion.

Consistent with this understanding, it may be noted that the enclosure 254 encloses most of the base 252 (other than the sealing surface 232) even though in various example implementations they are formed or molded as separate parts which are configured to step together. Accordingly, references to structures or functions related to the proximal portion 206, the distal portion 214, and/or the concave mid portion 224 should be understood as referring to the respective relative positions of the described portions of the blood collection module 102.

By way of example, in the depicted example, the vacuum generation chamber 208, the blood extraction chamber 216, and the pressure equalization channel 228 are all at least partially hollow sections included and formed in the respective proximal, distal, and mid portions of the base 252. Referring to the general location of the vacuum generation chamber 208 as being in the proximal portion 206 and the general location of the blood extraction chamber 216 as being in the distal portion 214 helps clarify that unlike existing designs where the vacuum generation chamber 208 and the blood extraction chamber 216 overlap to some degree, in the blood collection module 102, the vacuum generation chamber 208 and the blood extraction chamber 216 are located in geometrically separate portions such that in order for the air pressure to be equalized in the vacuum generation chamber 208 and the blood extraction chamber 216, a pressure equalization channel 228 between the vacuum generation chamber 208 and the blood extraction chamber 216.

At the same time, the vacuum generation chamber 208, the blood extraction chamber 216, and the pressure equalization channel 228 are all at least partially enclosed by the enclosure 254 and may therefore be referred to as being included in or comprised within the respective proximal, distal, and mid portions of the enclosure 254. Similarly, separate components (e.g., the vacuum piston, O-rings, lancet carrier, and so forth) which are located at the respective proximal, distal, and mid portions of the enclosure 254 and of the base 252, may also be referred to as being included in or comprised within such respective proximal, distal, and mid portions of either the base 252 and of the enclosure 254, based on the fact that such separate components are at least partially enclosed within such portions of the enclosure 254 end of the base 252 and should not be understood as necessarily being formed as part of the enclosure 254 or of the base 252.

The concave mid portion 224 includes a pressure equalization channel 228 configured to equalize reduced air pressure within the vacuum generation chamber 208, the blood extraction chamber 216, and a transfer module 104 coupled to the blood collection module 102. During blood collection, when the blood collection module 102 is attached to the skin 122 of the subject 116, the pressure equalization channel 228 is higher than the opening 235 and the skin 122 of the subject 116 is sealed to the sealing surface 232 by the skin adhesive 233 so that in response to the slide latch 136 being actuated by the lengthwise sliding motion, the pre-compressed volume expansion spring is released causing a partial vacuum to be generated and reduced air pressure to be equalized within the vacuum generation chamber, the blood collection chamber, and the transfer module to facilitate rapid blood flow downwards to the transfer module 104, e.g., a microtube 105.

Referring now to further improvements relating to illustrations intended to portray the accelerated blood flow of the apparatuses, modules, and methods disclosed herein FIG. 2I is an isometric view of a blood collection module 102 with an inset view linearly-arranged lancet strips 242 and an angled transfer module 244 being used for accelerated ergonomic self-collection of capillary blood. FIG. 2J is an isometric bottom view of blood collection module 102 component with a plurality of linearly-arranged lancet strips 242 configured to allow blood to flow from a plurality of rows of blood extraction slits 278 through one or more channels between the linearly-arranged lancet strips 242. FIG. 2K is an illustration of a top view, side view, and front view, of a lancet 213 such as used in the plurality of linearly-arranged lancet strips 242.

FIG. 2I depicts a blood collection module 102 placed on and searingly coupled to skin 122 at a collection site 120 of a body part such as an upper arm, of a subject 116. In various implementations, the plurality of linearly-arranged lancets strips 242 are configured to cause a plurality of rows of blood extraction slits 278 in the skin 122 to be generally aligned with a blood flow direction from the blood collection module 102 to the transfer module 104 to inhibit flow interference from edges of the blood extraction slits 278. In a simple example, depicting two rows of blood extraction slits 278, blood 126 is seen flowing from rows of blood extraction slits through the blood flow channel 246 (shown in FIG. 2F) into the transfer module 104, which may be a microtube 105.

Figure 3A:
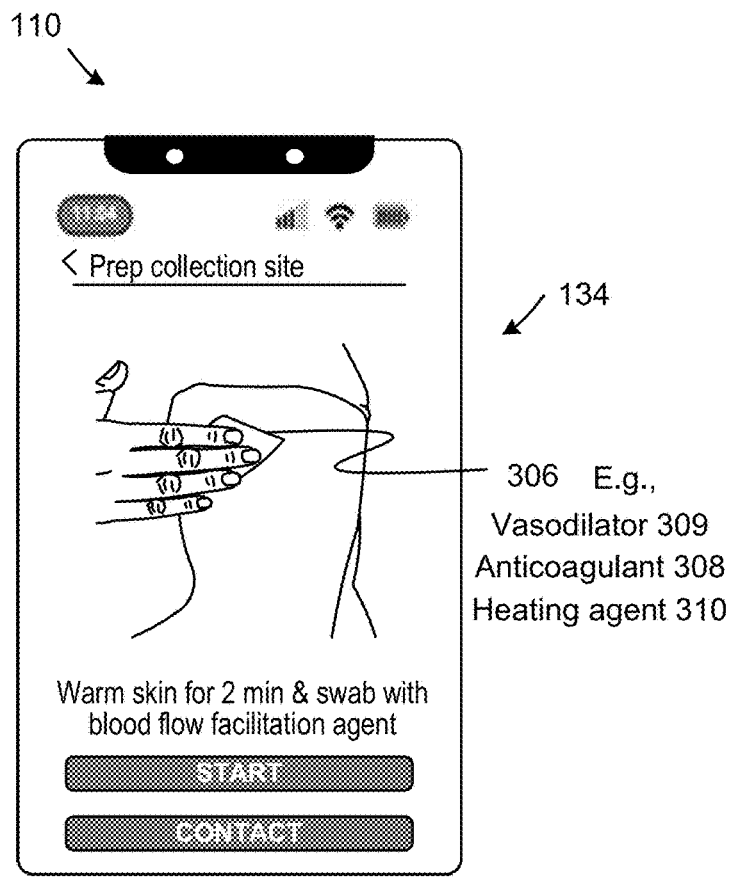
FIG. 3A is an illustration of an apparatus including a tracking module that provides onscreen communication for a collection site preparation step for performing accelerated ergonomic collection of capillary blood, according to one or more examples of the disclosure.
Figure 3C:
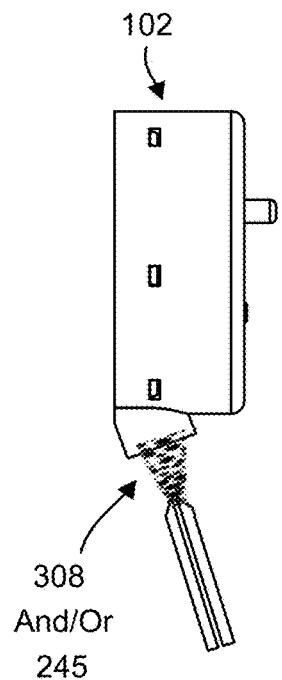
FIG. 3C is an illustration of a system and method that include a blood collection module preparation step for performing accelerated ergonomic collection of capillary blood, according to one or more examples of the disclosure.
Figure 3B:
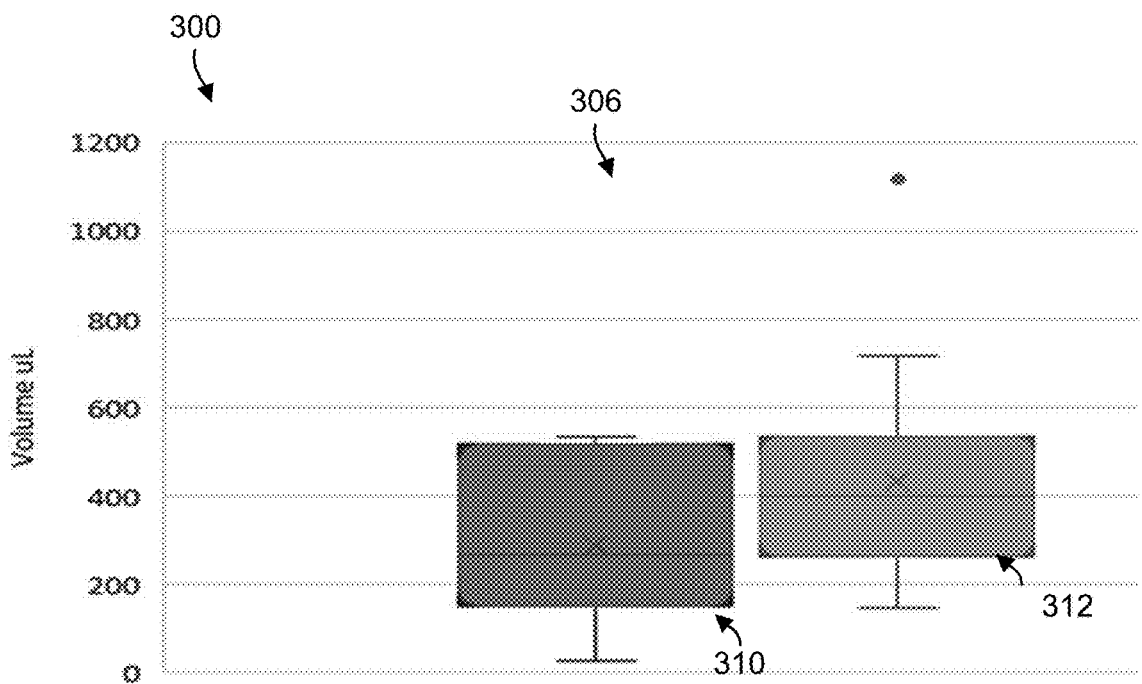
FIG. 3B is a chart comparing blood collection volumes for different collection site preparation types.

Before describing FIGS. 3A, 3B, and 3C, it may be helpful to refer again to certain functions of the system 100, as described above with respect to FIG. 1.

The accelerated ergonomic collection of capillary blood is significantly benefited by various mechanical features of the blood collection module 102. However, certain electronic, software, biochemical, and physical features may also enhance the accelerated ergonomic collection of capillary blood. For example, the process tracking module 108 may be configured to display various steps to be performed by the subject during the modular self-collecting of capillary blood to enhance accelerated blood flow and/or enhance economic usage of the blood collection module 102 and other components of the system 100.

For example, blood collection operational instructions (which may in certain examples be presented via onscreen communications 114 on the portable electronic device 110 such as depicted in FIG. 1) may be configured to provide beneficial instructions to the subject to prepare to collect the blood such as, running water over the arm from which blood is to be collected.

In some examples, a process tracking module 108 selectively displays certain instructions based on the type of transfer module 104 to be used, the type of test to be performed using the blood sample, and profile data for the particular subject. For example, an example operational instruction may describe how the blood collection module 102 is designed to be adhesively coupled to a region of skin 122 of a subject. In some implementations, the instructions may vary depending on the characteristics of the subject. For example, as mentioned above, for small children, a simple collection site may be found on a lower back region, or for animals, other body a suitable collection site may be found on vertical regions of skin which are shaved or otherwise hairless.

The blood collection module 102 is shipped with a release liner 237 (shown in FIG. 2A) which may be removed just prior to adhesively coupling the blood collection module 102 to the region of skin 122 of the subject.

Figure 5:
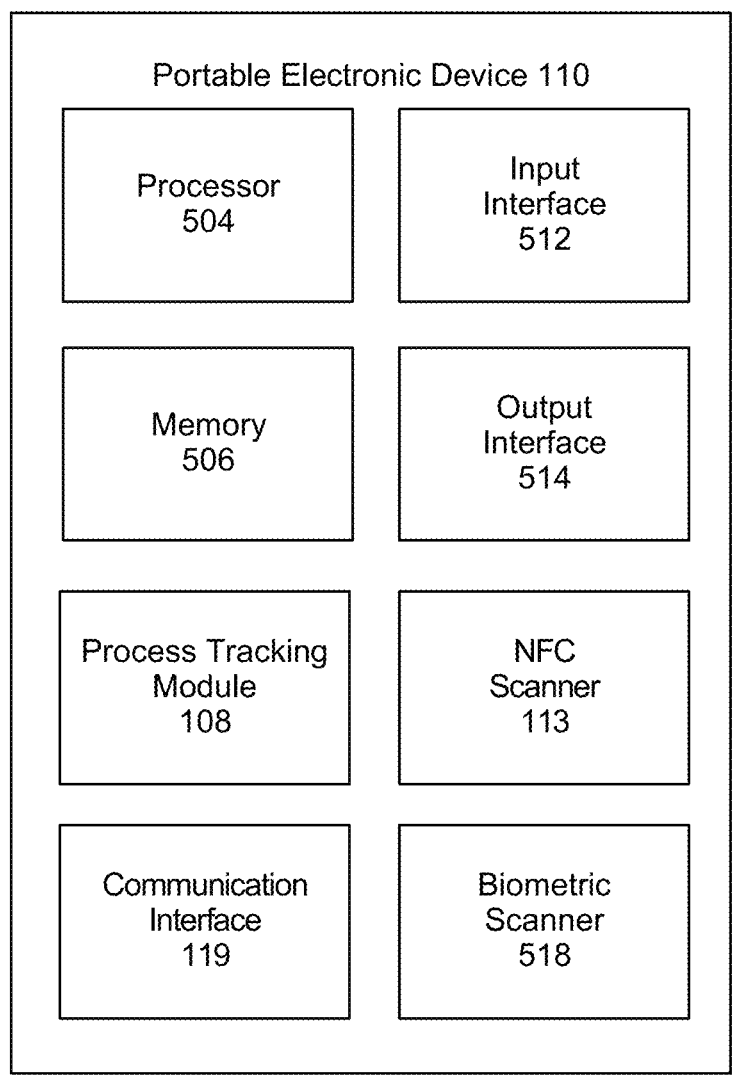
FIG. 5 is a schematic block diagram of a portable electronic device for providing communications related to use of the system for accelerated ergonomic collection of capillary blood, according to one or more examples of the disclosure.
Figure 7:
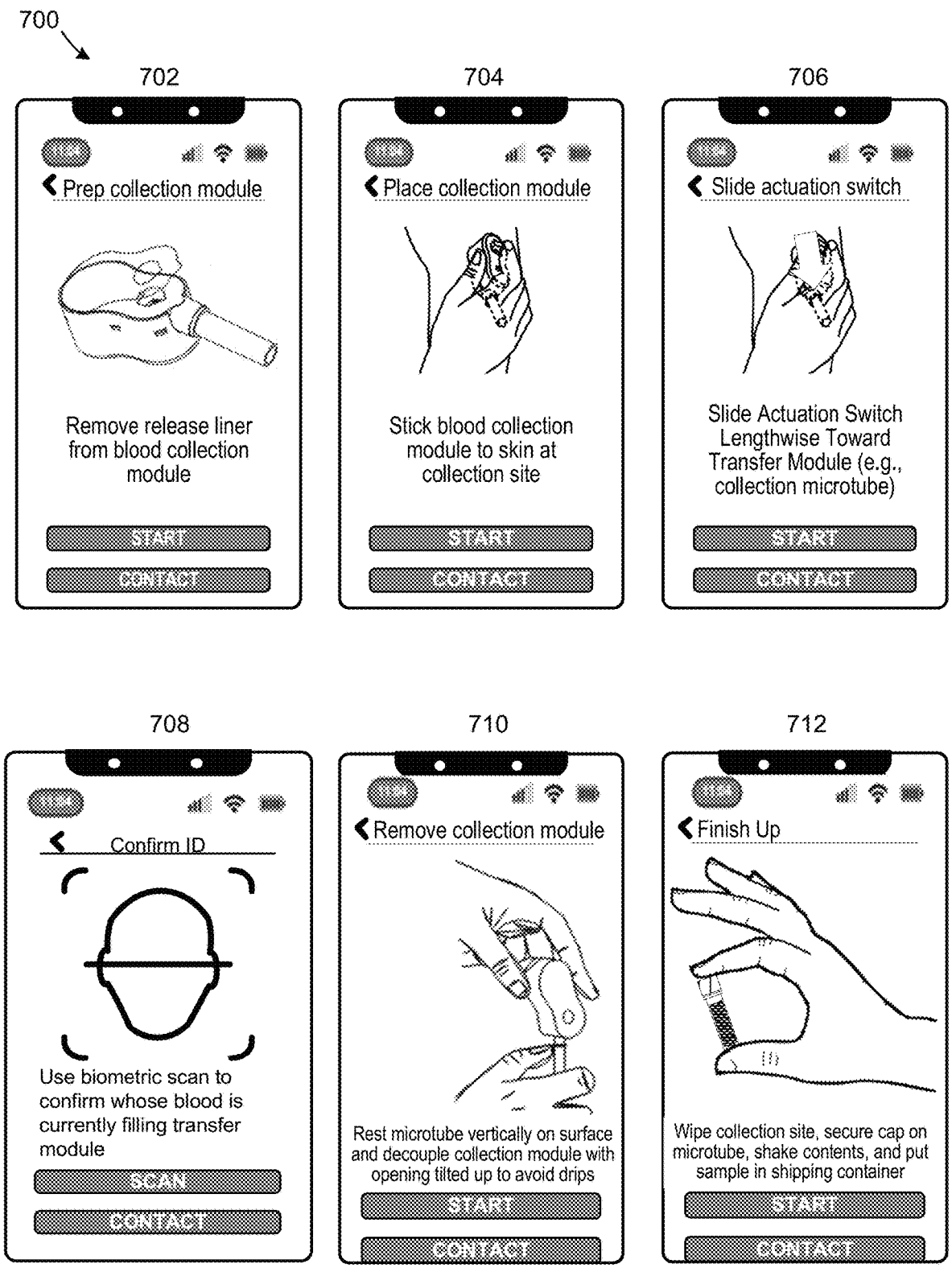
FIG. 7 depicts various onscreen communications associated with preparation, actuation, confirmation, and sample transportation steps for accelerated ergonomic collection of capillary blood, according to one or more examples of the disclosure.

In accordance with instructions provided by the laboratory or other home use blood collection kit provider, the subject follows instructions displayed by the process tracking module 108 (shown as a box with dashed lines in the portable electronic device 110 on FIG. 1 and described in more detail with respect to FIGS. 5, 6, and 7) to couple a transfer module 104 to the blood collection module 102 so that a collected blood level indicator such as a fill line on the blood collection module 102 or on the transfer module 104 is directly and readily visible within clear-sighted the subject as the subject faces towards the blood collection site of the region of skin. In some examples, the collected blood level indicator may be an onscreen communication that indicates sufficient blood has been collected based on elapsed timing of a time implemented by the process tracking module 108. As noted in the beginning of this application, modules such as the process tracking module 108 may be implemented or may include software components, hardware components or a combination of hardware and software components.

The angled transfer port 244 helps orient coupling of the transfer module 104 so that when coupled to the blood collection module 102 the distal end 207 of the transfer module 104 is lower than the proximal end 203 of the transfer module 104 which provides a gravity assist to aid the flow of blood 126 from the blood collection module 102 to the transfer module 104.

Moreover, with the blood collection module 102 adhesively coupled to a vertical region of skin 122 of the subject, the transfer module 104 or microtube 105 is positioned at an outward angle relative to the sealing surface so that it may be positioned to be viewed over portions of the subject's body while remaining stably coupled.

After the subject slides the slide latch 136 of the blood collection module 102 lengthwise towards the transfer module 104, he or she may tap the start button displayed in an onscreen communication 114, whereby, in certain examples, the process tracking module 108 determine a time that the blood collection was started for determining an approximate collection period. In various examples, the process tracking module 108 communicates with a data network 112 via the portable electronic device 110. Additional details about the structure and functions involved with the process tracking module 108 are described below with respect to FIGS. 5, 6, 7, and 8. After the blood is collected, the subject may remove the blood collection module 102 from the region of skin 122 and send the transfer module 104 to be appropriate receiving entity for further processing.

FIG. 3A is an illustration of an onscreen communication for a collection site preparation step for performing accelerated ergonomic collection of capillary blood, according to one or more examples of the disclosure. In some examples, prior to the act of coupling the blood collection module 102 to the region of skin 122 of a body part 117 (e.g., upper arm) of a subject 116, an onscreen communication 134 indicate that the step of including a blood flow facilitation agent 306 on the skin 122 of a body part 117 (e.g., upper arm) of a subject 116.

In various examples, prior to coupling the blood collection module 102 to the region of skin of a body part 117 (e.g., upper arm) of a subject 116, a blood flow facilitation agent. In certain examples, the blood flow facilitation agent includes a heat pack, a stream of warm water, a heated cloth, or similar heating agent. In various examples, the blood flow facilitation agent 306 may include an anticoagulant 308, a vasodilator 309, and/or a heating agent 310. In certain examples, the blood flow facilitation agent 306 includes lidocaine 312. Although lidocaine may have anesthetic effects as well, merely applying a topical anesthetic may be counterproductive. For example, some topical anesthetics such as those used for relief of tattoo pain and swell include lidocaine but also include epinephrine which is a vasoconstrictor which may reduce the volume and/or rate of blood collection.

FIG. 3B is a chart 300 of volume collected test results for different skin preparation protocols for accelerated ergonomic collection of capillary blood, according to one or more examples of the disclosure.

On a left portion of the chart 300, the results obtained are for a blood flow facilitation agent 306 that includes a heating agent 310 such as warm water or a warming object or substance. The results show that typical blood volumes collected ranged between about 115 microliters to 460 microliters which is higher than the volume that is collected when no blood flow facilitation agent is used.

On a right portion of the chart 300, the results are for a blood flow facilitation agent 306 that includes lidocaine 312. These results show that typical blood volumes collected ranged between about 190 microliters to 671 microliters which is higher than the volume that is collected when no blood flow facilitation agent 306 is used and is also even high than the volume collected using a heating agent 310, as the blood flow facilitation agent 306.

FIG. 3C is an illustration of a non-microfluidic blood flow channel anticoagulant atomization protocol for accelerated ergonomic collection of capillary blood, according to one or more examples of the disclosure. For example, a thin coating of anticoagulant 308 may be applied through the angled transfer port 244 using atomization or any suitable coating technique to reach the low-resistance non-microfluidic blood flow channel 246 of the blood collection module 102.

In various examples, the blood collection module 102 includes a skin adhesive 233 on a sealing surface 232 of the base 252 of the blood collection module 102. In various examples, the blood collection module 102 is configured to stably couple to a region of skin 122 of a subject. Certain aspects of the blood collection module 102 enhance its stability when coupled to a region of skin. In one or more implementations, a stabilizing aspect is that the diameter of the base 252 is at least as large as the height of the blood collection module 102. When a subject slides the slide latch 136, the sealing surface 232 being relatively wide at a bottom surface of the base 252 inhibits the blood collection module 102 from tipping or rocking.

In various implementations, the skin adhesive 233 that forms a sealing surface 232 at the bottom of the base 252 is adhesively coupled to the bottom surface of the base 252 so that it covers an open bottom portion of a pressure equalization channel 228. The skin adhesive 233 (depicted as a dot pattern in FIG. 2A) for adhesively sealing a bottom surface of the base 252 to the skin 122 of the subject 116 during the collection of blood 126.

In certain implementations, when the blood collection module 102 is provided to a subject, the skin adhesive 233 is covered by release liner 237 (depicted with a tab pulled up in FIG. 2A) that the subject is instructed to remove immediately before sticking the blood collection module 102 onto the skin 122 of the subject 116.

Preceding portions of the detailed description have highlighted regarding ergonomic features of the system 100 and the blood collection module 102.

However, the following portions of the detailed description provide additional information about how certain features of the system 100 and the blood collection module 102 may be used for accelerated collection of capillary blood such as for example the number and arrangement of the lancet strips, the preparation of the subject and the modules, and the use of certain types of transfer modules to facilitate additional operations such as plasma separation.

Beginning with acceleration of the blood extraction, FIG. 2E is a cross-sectional side view of a blood collection module 102 with a plurality of linearly-arranged lancet strips 242 for accelerated ergonomic collection of capillary blood, according to one or more examples of the disclosure.

In various examples, the blood collection module 102 includes a plurality of linearly-arranged lancet strips 242 which when triggered by a subject depressing the slide latch 136, is propelled downward to momentarily puncture and retract to produce micropunctures in the region of skin of the subject.

In certain examples, the plurality of linearly-arranged lancet strips 242 is coupled to a lancet carrier 240 that is biased by a lancet carrier spring 248. Prior to actuation, the lancet carrier spring 248 is held in a compressed state by one or more lancet carrier latches 274 that clip onto a foot 275 of the lancet carrier 240. When the slide latch 136 is actuated by a lengthwise sliding motion toward the angled transfer port 244, the lancet carrier latches 274 are unlatched (e.g., pulled away from the foot 275 of the lancet carrier 240 by a collar spring 272 pushing an extraction collar 270 to which the lancet carrier latches 274 are coupled, away from the foot 275 of the lancet carrier 240 so that they no longer catch on the lancet carrier foot 275). The spring force of the lancet carrier spring 248 propels the lancet carrier 240 downward causing the plurality of linearly-arranged lancet strips 242 to momentarily puncture and retract from the region of skin 122 of the subject. The term "momentarily" as used herein refers to a very brief period of time such as less than 1000 milliseconds, less than 500 milliseconds, or less than 250 milliseconds.

By causing the plurality of lancet strips to rapidly puncture and retract from the region of skin 122 at the collection site 120, the likelihood of pain being perceived by the subject may be reduced. Furthermore, the faster that blood starts flowing from the micropunctures through the low-resistance non-microfluidic blood flow channel 246 to the transfer module 104, the lower the likelihood is that the collective blood will start to clot.

The one or more implementations, there is an opening 235 in the sealing surface 232 of the blood collection module 102. The opening 235 forms a perimeter through which pass tips of a plurality of linearly-arranged lancet strips 242. More about the additional details about the plurality of linearly-arranged lancet strips 242 are described below with respect to FIGS. 2I, 2J, and 2K. The opening 235 is fluidically coupled to a low-resistance non-microfluidic blood flow channel 246 that passes through the angled transfer port 244. In various examples, the low-resistance non-microfluidic blood flow channel 246 is large enough that as blood 126 flows into the transfer module 104, the flow is self-venting meaning that no separate air return path is needed. In the depicted implementation, no separate air return path is needed. However, alternative implementations may include a low-resistance non-microfluidic blood flow channel 246 with a separate air return path (not shown).

In general, there is an inverse relationship between blood flow channel resistance and the blood flow rate—the higher the blood flow resistance, the slower the blood flow rate. Slower blood flow rate may lead to increased coagulation and/or reduced blood volume collected In some implementations, a maximum length of the low-resistance non-microfluidic blood flow channel 246 is less than a minimum inner diameter of the transfer module 104. A shorter length of the low-resistance non-microfluidic blood flow channel 246 minimizes the resistance. This represents a significant improvement over microfluidic designs where the length of the microfluidic channels is relatively long compared to an inner diameter of the collection container e.g., transfer module.

In various implementations, an inner minimum cross-sectional area of the low-resistance non-microfluidic blood flow channel 246 in the blood collection module 102 is at least 30% as large as the minimum inner cross-sectional area of the transfer module 104 through which blood 126 collected using the blood collection module 102 is configured to flow.

In various examples, prior to the act of coupling the blood collection module to the region of skin of a body part 117 (e.g., upper arm) of a subject 116, a blood flow facilitation agent. In certain examples, the blood flow facilitation agent includes a heat pack, a stream of warm water, a heated cloth, or similar heating agent. In various examples, the blood flow facilitation agent includes an anticoagulant 308 and/or a vasodilator 309. In certain examples, the blood flow facilitation agent includes lidocaine. Although lidocaine may have anesthetic effects as well, merely applying a topical anesthetic may be counterproductive. For example, some topical anesthetics such as those used for relief of tattoo pain and swell include lidocaine but also include epinephrine which is a vasoconstrictor and would likely reduce the volume and/or rate of blood collection.

As explained in more detail below with respect to the detailed description of FIG. 2I, 2J, the blood collection module 102 punctures and retracts from the skin 122 of the subject, after which capillary blood begins to flow into the opening 235 and from there through the low-resistance non-microfluidic blood flow channel 246 to the angled transfer port and transfer module 104 where it is collected.

One of the benefits of using a non-microfluidic blood flow channel for blood collection, such as the low-resistance non-microfluidic blood flow channel 246, is that the submillimeter dimensions of microfluidic channels may be more susceptible to clogging due to blood clotting. Furthermore, the submillimeter dimensions of microfluidic channels may result in inadequate blood flow rate from the blood collection module 102 to the transfer module 104. In addition to prolonging the blood collection duration for the subject, slower blood flow rates may increase the likelihood of blood clots forming. Moreover, using microfluidic channels especially in the presence of a partial vacuum or pressurized air increase the likelihood of hemolysis or similar damage to blood 126. Accordingly, in various examples, the low-resistance non-microfluidic blood flow channel 246 has minimum dimensions that are greater than submillimeter.

In some examples, the low-resistance non-microfluidic blood flow channel 246 include a friction reducing (e.g., lubricious) material that facilitates the flow of blood 126 through the low-resistance non-microfluidic blood flow channel 246. Various types of lubricious polymers may be used to form or coat the low-resistance non-microfluidic blood flow channel 246. The low-resistance non-microfluidic blood flow channel 246 may include a friction reducing material or coating. In some examples, the lubricious materials selected are also antithrombogenic to prevent formation of blood clots, which further facilitates smooth flow of the blood from the rows of blood extraction slits 278 in the skin 122 through the low-resistance non-microfluidic blood flow channel 246 to the transfer module 104.

As depicted in the enlarged inset shown in FIG. 2I, as blood 126 from rows of blood extraction slits 278 are produced by the multiple linearly-arranged lancet strips 242 (as discussed below with respect to FIG. 2J, 2I) of the blood collection module 102 fill the opening 235, it flows through the low-resistance non-microfluidic blood flow channel 246 towards the angled transfer port 244 which angles downward to a transfer module 104 thus displacing air which is in the transfer module 104. In turn, the displaced air flows above the blood 126 which equalizes the air pressure in the opening 235 and the transfer module 104 coupled to the blood collection module 102 so that the blood 126 can continue to flow down until the transfer module 104 is filled to a predetermined level.

FIG. 2D is a pre-actuation cross-sectional side view of a blood collection module 102 with a vacuum generation chamber 208 for accelerated ergonomic collection of capillary blood, according to one or more examples of the disclosure. In various examples, the vacuum generation chamber 208 holds a vacuum piston 262 that is biased by a precompressed volume expansion spring 210.

As depicted in FIGS. 2D-2E, in one or more examples, the slide latch 136 is mechanically coupled to the plurality of linearly-arranged lancet strips 242 and configured upon sliding lengthwise by a first predetermined distance toward the transfer module 104 to trigger a plurality of linearly-arranged lancet strips 242 to momentarily puncture and retract to produce rows of blood extraction slits 278 in the skin 122 of the subject 116.

Similarly, when the slide latch 136 is easily slid a second predetermined distance toward the transfer module 104, the precompressed volume expansion spring 210 is released and the volume of space within the vacuum generation chamber 208 begins to increase due to the vacuum piston 262 being pushed away from the sealing surface 232 thus reducing air pressure inside the expanded vacuum generation chamber 208 and at the opening 235 above the rows of blood extraction slits 278 relative to ambient pressure. This reduction of pressure above the rows of blood extraction slits 278 in the skin may beneficially assist in drawing blood out of the skin and into the angled transfer port 244.

In some implementations, a plurality of linearly-arranged lancet strips 242 are configured as two parallel rows such as depicted in FIGS. 2I, 2J. However, some implementations may be configured with more than two rows. In certain implementations, the linearly-arranged lancet strips 242b, may be configured to have one or more V shapes such that the downstream or distal portions of the lancet strips 242b are closer together than the proximal portions of the same lancet strips 242b. This arrangement may in certain circumstances enhance the accelerated blood flow by guiding the blood flows from the individual lancet strips 242b to flow together.

Referring to the relative position of the slide latch 136 in the partially actuated state in which the lancet strips 242 are triggered to punch her the skin 122 of the subject 116 as depicted in FIG. 2E and the position of the slide latch 136 in the fully actuated state in which a vacuum is generated in the vacuum generation chamber 208 by the movement of the vacuum piston and the corresponding O-ring 264 within the vacuum generation chamber 28 by the expansion of the precompressed volume expansion spring 210, these relative positions are mechanically selectable by using differently configured slide latches 136 in which the predetermined positions for generating the vacuum and/or triggering the lancet strips of the slide latch 136 are selected based on where the blocking elements of the slide latch 136 are formed relative to the spring-loaded elements that are held in place by the respective blocking elements of the slide latch 136.

In other words, by selecting a differently configured slide latch 136 the vacuum generation and lancet strips triggering may be configured to occur with the lancet strips triggering first in the vacuum generation occurring second as depicted in FIGS. 2E and 2F in some implementations. In other implementations, the vacuum generation and lancet strip triggering may be configured to occur substantially at the same time. In further implementations, the vacuum generation may be configured to occur prior to the lancet strips triggering by selecting a slide latch 136 configured to release the vacuum piston 262 pressing against the precompressed spring 210 prior to releasing the extraction collar 270 to allow the lancet strips 242 to be triggered.

In some examples, the plurality of linearly-arranged lancet strips 242 comprises a plurality of lancet strips coupled to a lancet carrier 240 that is spring-loaded and that holds the ring of flat lancets latched in a retracted position prior to the lengthwise sliding of the slide latch 136; and propels the ring of flat lancets to momentarily puncture and retract from the region of skin 122 in response to the lengthwise sliding of the slide latch 136.

The inventors of the subject matter of the present disclosure have identified various factors that affect blood flow rate from wounds and thereby affect blood collection rate. Certain factors that increase blood flow rate may also increase the likelihood of a subject experiencing pain associated with the production of rows of blood extraction slits in the skin.

For example, a greater number of lancets in the linearly-arranged lancet strips may stimulate greater blood flow but may allow increase the likelihood of one or more of the lancets contacting one or more nerve endings thereby increasing the likelihood of the subject experiencing pain.

In certain implementations, such as for example, as depicted in FIG. 2J, the linearly-arranged lancet strips 242 may include from about 3 to about 10 evenly distributed flat lancets of at least 1.5 mm in length to facilitate probabilistic penetration of a plurality of the lancets to a penetration depth that facilitates blood flow from sub-epidermis capillaries. As used herein the term "about" with reference to a whole number means plus or minus ten percent rounded to the nearest integer.

Getting a good blood flow rate for a blood is an initial objective but an efficacious system for accelerated ergonomic collection of capillary blood should include improvements to transfer modules and methods that facilitate rapid, safe, and efficient transfer of blood components for analysis and other uses.

Figure 4A:
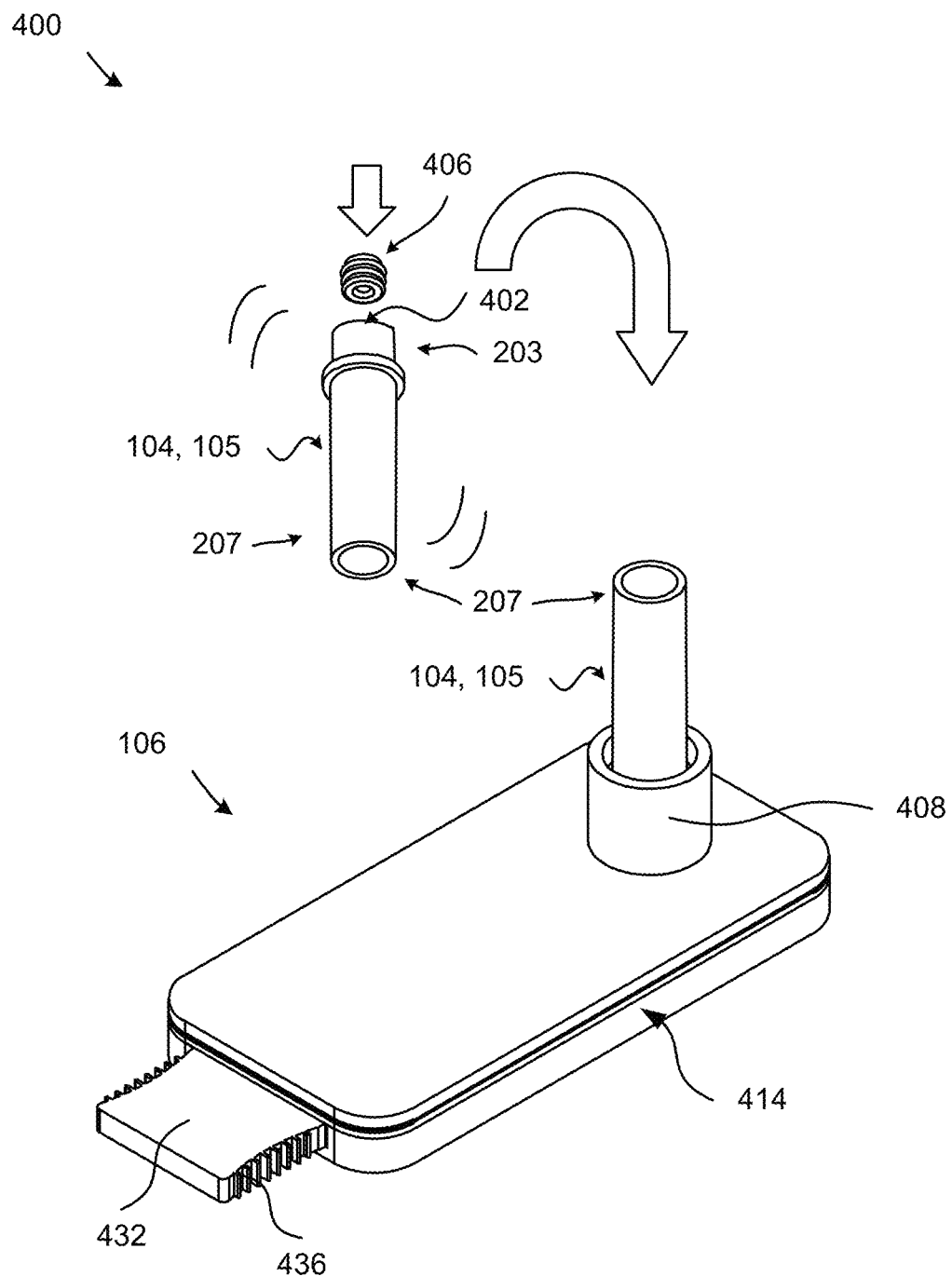
FIG. 4A is an isometric view of an apparatus that includes a plasma separation module for separation of plasma from capillary blood collected by a blood collection module, according to one or more examples of the disclosure.

FIG. 4A is an isometric view of an apparatus 400 that include an instance of a plasma separation module 106 for separation of plasma from capillary blood collected by a blood collection module 102 and transferred to a transfer module 104, e.g., a microtube 105, according to one or more examples of the disclosure.

Figure 4B:
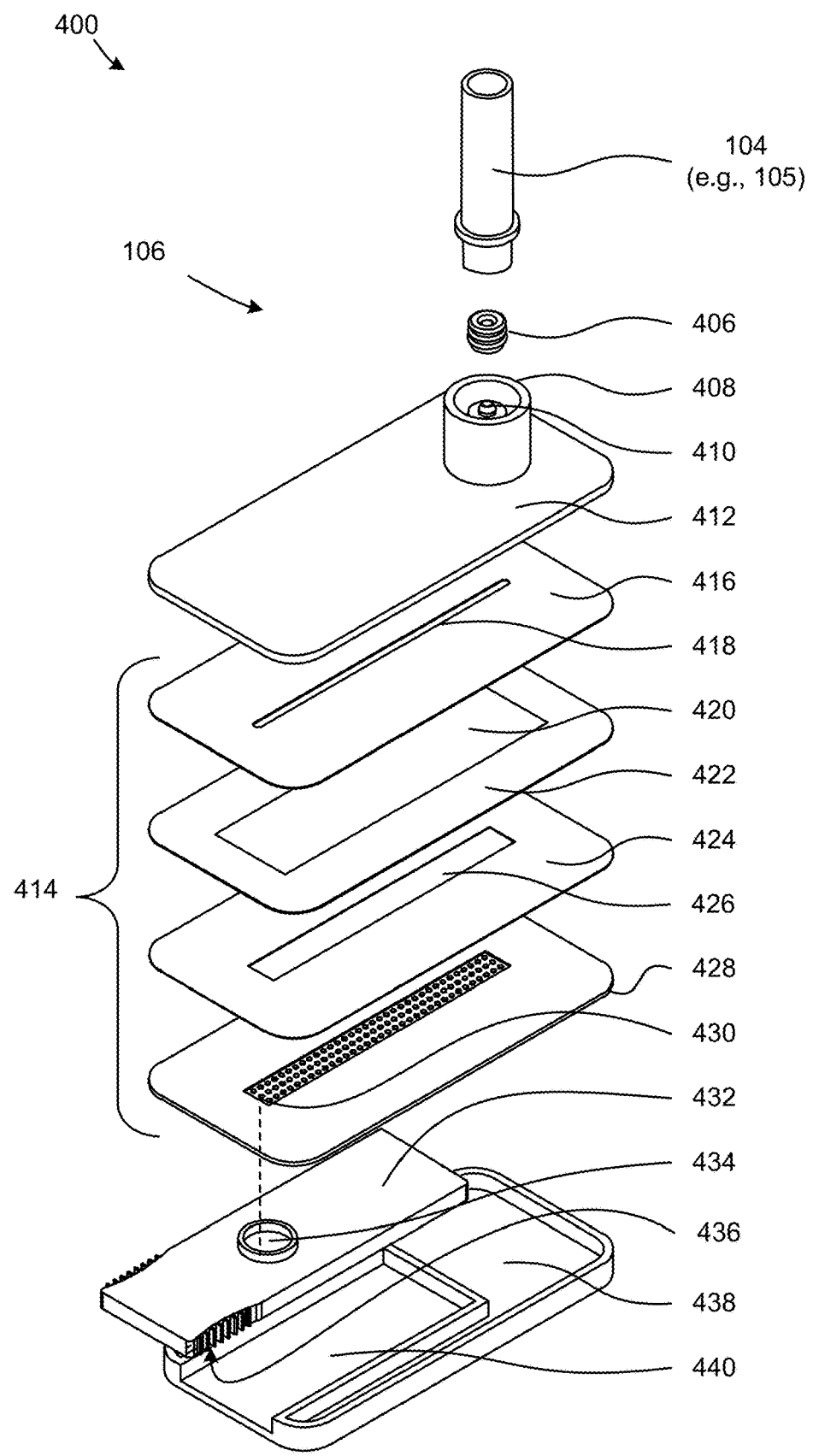
FIG. 4B is an exploded isometric view of various layers and components of a plasma separation module for separation of plasma from capillary blood collected by a blood collection module, according to one or more examples of the disclosure.

FIG. 4B is an exploded view of the plasma separation module 106. In the following description, various problems solved by the plasma separation module 106 are described. The structures and functions of the plasma separation module 106 are described including interaction between the plasma separation module 106 and other components of the system 100.

Certain existing types of plasma separation apparatuses use centrifugation or pressurized blood flow through tubing to a plasma separation filter. However, such apparatuses may be unsuitable for home use due to the size, complexity, and cost. Furthermore, such apparatuses and methods may induce hemolysis i.e., the rupture of red blood cells. For testing purposes, hemolysis may reduce sensitivity of diagnostic tests or may lead to a decrease in the accuracy of the test results.

The structures and functions of the plasma separation module 106 disclosed herein may facilitate broadly available and efficient separation of plasma from whole blood at home or in other locations using simple steps that are easy to follow by persons with little training.

For example, in certain implementations, a subject may collect capillary blood from a region of skin on an upper arm, shoulder, forearm, or other suitable region of skin of a subject, using the blood collection module 102, as described above with respect to FIG. 1, and FIGS. 2A-2I. In some implementations, the subject may transfer the blood to transfer module 104, e.g., a microtube 105, via the angled transfer port 244. In various implementations, the subject may then insert an elastomeric plug 406 with a compression activated aperture so that in a relaxed state the elastomeric plug 406 allows the transfer module 104, e.g., the microtube 105, to be shaken and mixed with an anticoagulant without spillage.

With the elastomeric plug 406 inserted, the transfer module 104, e.g., the microtube 105, may then be inverted such that an outer diameter at the end of the transfer module 104, e.g., the microtube 105, with the elastomeric plug 406 fitted snugly within an inner diameter of a blood input port 408 formed in a top plate 412 of the plasma separation module 106.

In various implementations, a subject may initiate transfer of blood from the (plugged) transfer module 104, e.g., the microtube 105, into the plasma separation module 106 by pressing the elastomeric plug 406 of the transfer module 104, e.g., the microtube 105, (which is now inverted) down on a mating feature 410 which has a center blood flow channel leading to lower layers of the plasma separation module 106. In one or more example implementations, the mating feature may contain a needle which pierces a membrane in the elastomeric plug thus allowing blood to flow, down through the channel in the top plate.

In certain example implementations, the elastomeric plug 406 may have a one-way valve that is opened by a tube protruding from the mating feature 410. The subject may then continue to gently press down on the inverted distal end of the transfer module 104, e.g., the microtube 105, towards the plasma separation module 106 until it snaps into place. In various examples, the action of pressing the transfer module 104, e.g., the microtube 105, down may slide the elastomeric plug farther into the container, evacuating any blood 126 and creating positive pressure which may be used to drive the plasma separation process. In certain example implementations, after a predetermined amount of time sufficient to allow transfer of separation of a predetermined volume of plasma, such as for example, 500 microliters, the subject removes a plasma cartridge 432 containing the separated plasma from a drawer-like compartment in a base plate 438 of the plasma separation module 106.

In various implementations, the plasma separation module 106 includes a multilayer laminate 414 below the top plate 412 and above the base plate 438 of the plasma separation module. By way of example, the multilayer laminate 414 may include four layers that form a blood-processing portion of the plasma separation module 106 to facilitate efficient plasma separation.

In some implementations, immediately below the top plate 412, a top layer of the laminate is formed using an upper thin film adhesive 416 with a blood-spreading channel 418 and passes through the upper thin film adhesive 416 so as to facilitate even spreading of the blood 126 across the length of the channel thus reducing the likelihood of clotted or coagulated blood accumulating in the region directly below the opening to the transfer module 104, e.g., the microtube 105. The blood the passes through down through the blood-spreading channel 418 to a plasma separation membrane 420.

In the depicted implementation, the plasma separation membrane 420 is surrounded by a plasma separation membrane frame 422 which also acts as a vertical spacer to prevent the plasma separation membrane 420 from being pushed too tightly against the upper thin film adhesive 416 above the plasma separation membrane 420 or against a lower thin film adhesive 424 below the plasma separation membrane 420. In various implementations, the plasma separation membrane 420 is a highly asymmetric hydrophilic microfiltration membrane with high surface porosity that facilitates rapid separation of high-quality plasma with greater than 80% plasma yield. One example of a suitable plasma separation membrane is obtainable from Pall Corporation of Port Washington, New York.

The lower thin film adhesive 424 includes a plasma channel 426 through which separated plasma flows downward towards a collecting plate 428. An outer portion of the lower thin film adhesive 424 seals the bottom portion of the plasma separation membrane frame 422 to a top surface of a collecting plate 428.

In certain examples, a centerline portion of the collecting plate 428 includes an array of raised bumps or cylinder-like standoffs that inhibit the plasma separation membrane 420 from sticking to a planar top surface of the collecting plate 430. In other words, on to the plasma separation module, even when the transfer module 104, e.g., the microtube 105, is being pushed down, the array of standoffs provides open spaces between the standoffs through which plasma can flow as it moves towards an outlet hole that passes down through the collecting plate 430 to be dispensed into a dispensing opening 434 in a top portion of the plasma cartridge 432.

In various examples, the plasma cartridge 432 holds collected plasma and is configured to slide in or out of the drawer-like compartment 440 of the base plate 438 of the plasma separation module 106. A pull 436 with a concave portions and ridges on both sides allows the plasma cartridge to be easily inserted and extracted from plasma separation module 106. In certain examples, the plasma cartridge 432, containing separated plasma may be inserted directly a plasma analysis instrument.

Thus, the structures and processes described herein for separation of plasma from peripheral broad facilitate efficient and simple collection of blood plasma that can be performed in a variety of locations without specialized personnel or equipment other than the modules described herein.

FIG. 5 is a schematic block diagram of an apparatus 500 that includes a portable electronic device 110 for implementing accelerated ergonomic collection of capillary blood, according to one or more examples of the disclosure.

The portable electronic device 110 may be a cell phone, a smart phone, tablet, a laptop computer, or similar device. The portable electronic device 110 in various examples includes a processor 504, a memory 506 that contains code and/or data related to accelerated ergonomic collection of capillary blood. For example, in certain examples, the process tracking module 108 is implemented as code executable by the processor 504. In various examples, the portable electronic device 110 includes an input interface 512 and an output interface 514 in some examples, a touchscreen display provides some input interface functions and some output interface functions.

In some examples, the portable electronic device 110 includes a communication interface 119 that may include one or more transceivers for such as mobile telecommunications transceivers, Bluetooth transceivers, and so forth.

In various examples, the portable electronic device 110 includes an NFC scanner 113 which is used by the process tracking module 108 to perform NFC scans of NFC tags 135 attached to the blood collection module 102 and/or to the transfer module 104. In some examples, a subject may initiate scanning by touching a display button labeled "scan NFC" and/or by tapping the portable electronic device 110 lightly against the NFC tag 135.

In some examples, the portable electronic device 110 includes a biometric scanner 518 that is accessible by the process tracking module 108 one or more optical cameras, and software for analyzing fingerprints, iris prints, facial recognition, and/or other biometric measurements that may be useful for confirming the identity of the subject. Additional detail regarding the structure and function of the blood collection module 102 is provided throughout this disclosure and in particular with respect to FIGS. 2A, 2B, 2C, 2D, 2E, 2F, 2G, 2H, 2I, 2J, 2K, It may be noted that although various advantages are provided by the inclusion in the system 100 of the process tracking module 108, in some examples, the blood collection module 102 and the transfer modules 104 are usable for collecting blood in a manual mode without the inclusion of the process tracking module 108.

FIG. 6 is an illustration of a subset 600 of onscreen communications 114 related to confirming proper use of the system for accelerated ergonomic collection of capillary blood, according to one or more examples of the disclosure.

Depicted in FIG. 6, is an onscreen communication 137, in which a user is instructed to enter the name of the subject 116 from whom blood is being collected e.g., using the system 100. In some example implementation, the user is further instructed to scan each module being used such as the blood collection module 102, the transfer module 104, and/or the plasma separation module 106. Scanning the modules may be done using an NFC scanner such as the NFC scanner 113 depicted in FIG. 5.

A further onscreen communication 138 include information selected from a manufactured date of the one or more selected modules, a expiry date of the one or more selected modules, a product identification number of the one or more selected modules, a device type of the one or more selected modules, blood collection timing information for the one or more selected modules, blood preservation and storage parameters for the one or more selected modules, shipment parameters for the one or more selected module, and combinations thereof. Communicating blood collection parameters 605, such as for example, those listed in onscreen communication 137, 138 of FIG. 6 or other parameters related to blood collection, enables the subject to determine whether the information matches expected information conveyed by others such as healthcare providers, requesting laboratory, insurer, and so forth.

FIG. 7 is an illustration of a group 700 of onscreen communications associated with preparation, actuation, confirmation, and sample transportation steps for accelerated ergonomic collection of capillary blood, according to one or more examples of the disclosure. In various examples, operational instructions such as those depicted in group 700 may be presented as onscreen communications 114 (such as 702, 704, 706, 708, 710, and 712 (or in certain implementations may be presented as printed instruction panels) for tracking accelerated ergonomic collection of capillary blood, according to one or more examples of the disclosure and, The onscreen communications may relate to preparation of the subject, preparation of the blood collection module or other apparatuses, operation and/or actuation of the blood collection module or other apparatuses, confirmation the subject, the collected blood and/or the apparatuses used to collect the blood or to separate plasma or perform other accelerated ergonomic collection of capillary blood. Certain instructions may provide information about sample transportation steps for accelerated ergonomic collection of capillary blood, according to one or more examples of the disclosure.

In various examples, a module preparation onscreen communication 702 describes an example of a blood collection module preparation step for performing accelerated ergonomic collection of capillary blood. Although the depicted example in the module preparation onscreen communication 702 describes removing a release liner from the blood collection module, other module preparation steps may be communicated such as information helpful to confirm that the right type of transfer module or microtube is prepared and available to couple to the transfer port of the blood collection module. In some examples, the blood collection module preparation steps may include information about and packaging, handling of the blood collection module.

The instructions may also include information about selection of a suitable collection site based on the type of subject from whom blood is being collected. For example, if the subject is an animal, the onscreen communication 702 may provide information about various locations on different body parts of the animal that may provide optimal results for blood collection. This could include information such as how to prepare the blood collection module to stick to the skin of the subject animal at a selected collection site.

A second depicted onscreen communication 704 provides information related to placing the blood collection module at the collection site.

A third depicted onscreen communication 706 provides information related to actuating the blood collection module placed at the collection site.

A fourth depicted onscreen communication 708 provides information related to biometric scanning to confirm information about the person on which the blood collection module is used.

A fifth depicted onscreen communication 710 provides information related to spill-free decoupling of the transfer module from the blood collection module.

A sixth depicted onscreen communication 712 provides information related to transportation of the transfer module.

Figure 8:
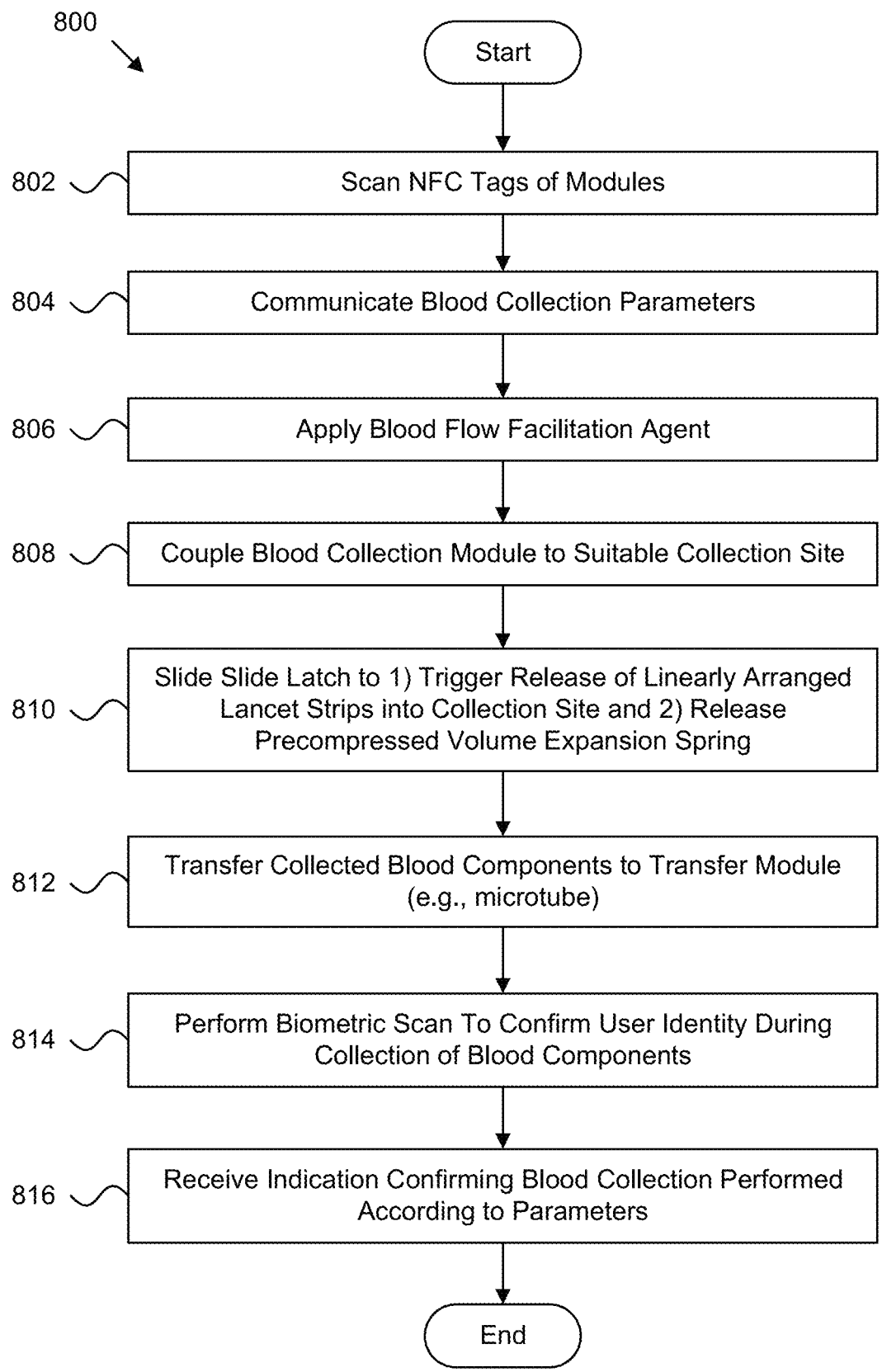
FIG. 8 is schematic flow chart diagram of a method of accelerated ergonomic collection of capillary blood, according to one or more examples of the disclosure.

FIG. 8 is schematic flow chart diagram of a method 800 of accelerated ergonomic collection of capillary blood, according to one or more examples of the disclosure. In various implementations, the method 800 begins and includes scanning 802 an NFC tag coupled to one or more modules for blood collection. For example, as depicted in a module preparation onscreen communication 702 shown in FIG. 7, the subject may enter her name and may be instructed to scan NFC tags of a blood collection module and a transfer module that will be used to collect and transfer the blood (e.g., for processing at a laboratory).

The method 800 continues and includes communicating 804 one or more blood collection parameters to a subject undergoing blood collection. For example, as depicted in onscreen communication 137, 138 in FIG. 6, in certain implementations, the blood collection parameters include information selected from a manufactured date of the one or more selected modules, a expiry date of the one or more selected modules, a product identification number of the one or more selected modules, a device type of the one or more selected modules, blood collection timing information for the one or more selected modules, blood preservation and storage parameters for the one or more selected modules, shipment parameters for the one or more selected module, and combinations thereof. Communicating blood collection parameters 605, such as for example, those listed in onscreen communication 137, 138 of FIG. 6 or other parameters related to blood collection, enables the subject to determine whether the information matches expected information conveyed by others such as healthcare providers, requesting laboratory, insurer, and so forth.

In certain examples, the method 800 continues and includes applying 806 a blood flow facilitation agent to the region of skin of the subject to which the blood collection module will be coupled for blood collection.

One or more examples of a blood flow facilitation agent include a heat pack, a stream of warm water, a heated cloth, or similar heating agent. For example, certain types of reusable heat packs called snap heat pads, click heat pads, thermopacks, or similar, contain phase change materials such as sodium acetate that is in a supercooled liquid state at room temperature so that when a metallic triggering device such as a metal disc within the pad is flexed, the supercooled liquid begins to freeze and releases heat thus warming up to a temperature of about 54° C. Such heat packs are non-toxic, reusable, and widely available and may be packaged so as to act as a safe and consistent blood flow facilitation agent.

In various examples, the method 800 include applying 806 a blood flow facilitation agent comprising an anticoagulant 308 and/or a vasodilator 309 to the skin 122 at or around the collection site 120 prior to the act of coupling 808 the blood collection module to the region of skin of a body part 117 (e.g., upper arm) of a subject 116. In certain examples, the blood flow facilitation agent includes lidocaine. Although lidocaine may have anesthetic effects as well, merely applying a topical anesthetic may be counterproductive. For example, some topical anesthetics such as those used for relief of tattoo pain and swell include lidocaine but also include epinephrine which is a vasoconstrictor and would likely reduce the volume and/or rate of blood collection.

The method 800 continues and include coupling 808 a blood collection module to a region of skin of a subject with the body part 117 (e.g., upper arm) of a subject 116 resting in a substantially horizontal position. In some example implementations, the blood collection module is sealed during blood collection to the region of skin of the subject using an adhesive. In certain examples, the blood collection module includes a strap, band, cuff, sleeve, cincture, or similar flexible fastening mechanisms that facilitates secure coupling of the blood collection module to the region of skin of the subject.

In some examples, the flexible fastening mechanism enables greater blood flow rate and/or volume to be achieved during collection, e.g., by allowing the subject to move the arm in a pattern that facilitates blood flow, such as for example, a circular motion, a windmill motion, arm circumduction, shoulder circumduction, a swinging motion, or similar motion, immediately before or during (e.g., after the step of coupling 808 the blood collection module to a suitable collection site as described below) collection of blood using the blood collection module.

Positioning the blood collection module horizontally or at an acute angle relative to a surface on which the arm rests facilitates easier actuation of the blood collection module by providing a stable support for the arm of the subject which in turn provides stable support for the blood collection module. Furthermore, such positioning enables the blood collection module to be directly and readily visible within clear-sighted the subject as the subject faces towards the collection site 120 in the skin 122 of the subject 116. Likewise, as illustrated in FIG. 2A transfer module connected to the angled transfer port 244 so that the blood flow is assisted by gravity or by centrifugal force.

The method 800 continues and includes sliding the slide latch 136 of the blood collection module 102 with a lengthwise motion towards a transfer module 104 and triggering a momentary puncture and retraction to produce multiple rows of blood extraction slits in the region of skin 122 of the subject 116. The method 800 continues and includes transferring 812 blood components and/or reagents from an opening of the blood collection module to a transfer module 104. The method 800 continues and includes performing 814 a biometric scan to confirm the identity of subject in a usage session that includes collection of the blood components from the subject.

In some examples, the process tracking module is optionally configured to perform the biometric scan to confirm subject identity within a predetermined time period that also includes scanning the NFC tag using the same device used for performing the biometric scan. For example, because the blood collection module is coupled to the region of skin of the subject, a biometric scan such as a facial recognition scan can be performed within the same predetermined time period that the NFC tag is being scanned by the same device (e.g., a smart phone, a tablet, and the like). For blood tests where it is important to securing ensure the identity of the subject from who blood is being collected (e.g., drug test, medical testing, and so forth), the secure coupling to the shoulder or forearm of the subject is useful because either the front-facing camera, the back-facing camera, or fingerprint scanner, of the device may capture biometric measurements (e.g., facial, iris, or fingerprint scan" while within a distance near enough to perform the NFC scan of the blood collection module.

The method 800 continues and includes receiving 816 an indication 607 from subject 116 indicating whether the blood collection was performed according to the communicated blood collection parameters which may be considered part of the reported results for the subject 116.

In various implementations, individual acts of the method 800 or combinations of acts of the method 800 for modular self-collecting of capillary blood may be performed using the system 100, the blood collection module 102, and/or the transfer modules 104 including the microtube 105, the plasma separation module 106, a dried blood module (not shown), a dried plasma module (not shown), and/or a reagent adder module (not shown).

Various types of plasma separation membrane 420 may be obtained from Pall Corporation of Port Washington, NY, Cobetter Filtration Equipment Co., Ltd of Hangzhou, China, or Fukae-Kasei Co., Ltd, of Kobe Japan, or similar suppliers.

Figure 9:
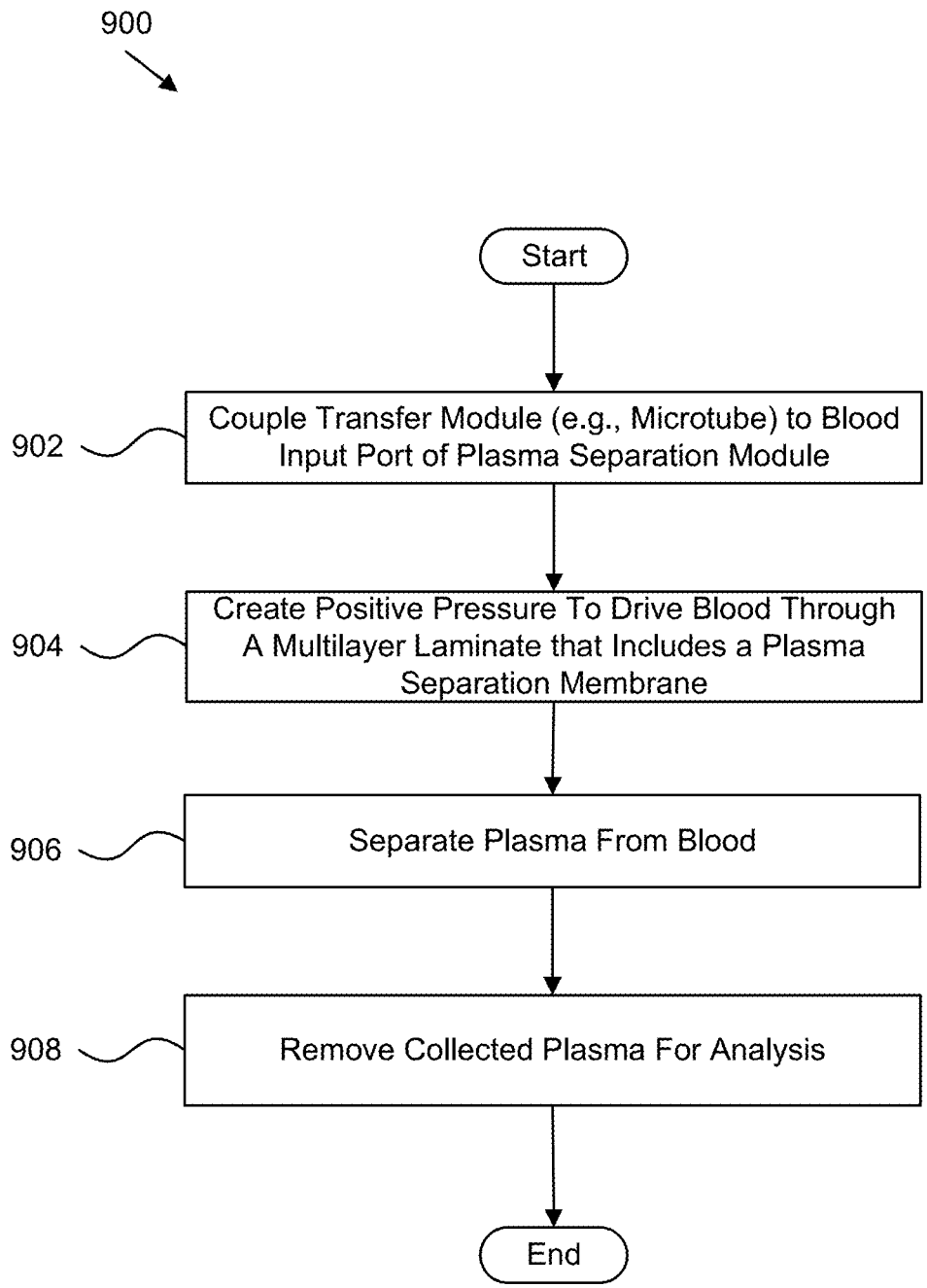
FIG. 9 is schematic flow chart diagram of a method of performing plasma separation following accelerated ergonomic collection of capillary blood, according to one or more examples of the disclosure.

FIG. 9 is schematic flow chart diagram of a method 900 of performing plasma separation following accelerated ergonomic collection of capillary blood, according to one or more examples of the disclosure.

In various examples, the method 900 begins and includes coupling 902 a transfer module 104, such as for example, the microtube 105 at blood input port 408. It may be noted that in certain implementations, the blood input port 408 of the plasma separation module 106 is configured to fluidically seal around an outside perimeter of the transfer module 104 (e.g., a microtube 105) using technology that includes coupling and structures such as an O-ring which described above with respect to the angled transfer port 244 of the blood collection module 102.

The method 900 continues and in one or more examples includes creating 904 a positive pressure to drive blood through a multilayer laminate that includes a plasma separation membrane. In some examples, creating 904 the positive pressure is accomplished by pressing down on a transfer module, e.g., the microtube 105 in an inverted position) to slide an elastomeric plug into the transfer module, creating positive pressure which may be used to drive the blood 126 through a multilayer laminate that includes a plasma separation membrane such as described above with respect to FIG. 4A and FIG. 4B.

In certain example implementations, this is accomplished by a user pressing down on a transfer module in an inverted position, such as described above which may include a microtube 105 having standardized dimensions such as a Microtainer® available from Becton, Dickinson and Company, or a compatible microtube.

In some implementations, the transfer module 104 comprises: a transfer opening 402 at the proximal end 203 of the transfer module 104, e.g., the microtube 105, with an inner diameter of about 10 mm and an outer diameter of about 13 mm; and a prepackaged additive selected to mix with the capillary blood to facilitate performance of one or more predetermined laboratory tests.

Using a transfer module 104 that is compatible with the system 100 and apparatus 200 as described above respect to FIGS. 1 and 2A-2I extends the benefits of accelerated collection of capillary blood by also accelerating the transfer process from the blood collection module 102 to the plasma separation module 106 using the same transfer module for the entire process. On the other hand, in some examples, the dimensions of the transfer module 104 may be different from that of a microtube 105.

The method 900 continues and includes separating 906 plasma from the blood. In various implementations, this is accomplished through the structures and functions of the multilayer laminate 414 described above with respect to FIG. 4A and FIG. 4B.

The method 900 continues and includes removing 908 the collected plasma for analysis. In various examples, this may be performed by removing a plasma cartridge or 32 containing the separated plasma from a drawer-like compartment 440 in a base plate 438 of the plasma separation module 106 described above with respect to FIGS. 4A and 4B.

In certain examples, after the plasma is collected, the plasma separation module 106 may be discarded according to applicable guidelines. Beneficially, a single-use plasma separation module may be used effectively without concerns about buildup of blood cell components that reduce the effectiveness of the plasma separation membrane 420.

Examples and implementations may be practiced in other specific forms. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

Clauses describing various implementations or embodiments of the present disclosure are provided below.

Clause 1. An apparatus 200 comprising: a blood collection module 102 that includes: a proximal portion 206 comprising a vacuum generation chamber 208 formed in a base 252, a vacuum piston 262, a precompressed volume expansion spring 210, and a slide latch slot 212 formed in an enclosure 254; a distal portion 214 comprising a blood extraction chamber 216 formed in the base 252 and configured to collect blood 126 from a collection site 120 in skin 122 of a subject 116; a concave mid portion 224 formed in the enclosure 254 between the proximal portion 206 and the distal portion 214 of the enclosure 254 to facilitate secure holding of the blood collection module 102 between two digits of a hand 123, the concave mid portion 224 further comprising a pressure equalization channel 228 formed in the base 252 and configured to equalize reduced air pressure within the vacuum generation chamber 208, the blood extraction chamber 216, and a transfer module 104 coupled to the blood collection module 102; a sealing surface 232 at a subject-facing portion of the blood collection module 102 and is configured to stably seal the blood collection module 102 to the skin around the collection site 120; a lancet carrier 240 disposed within the distal portion 214 and comprising a plurality of linearly-arranged lancet strips 242 wherein, in response to the lengthwise sliding motion of the slide latch 136, the lancet carrier 240 fires the plurality of linearly-arranged lancet strips 242 to momentarily puncture and retract from a plurality of rows of blood extraction slits 278 in the collection site 120; and an angled transfer port 244 disposed at the distal portion 214 of the blood collection module 102 and configured to allow the blood 126 to flow from the collection site 120 through a low-resistance non-microfluidic blood flow channel 246 to the transfer module, the angled transfer port 244 extending outward from the blood collection module 102 and being angled away from the subject 116 at an acute angle of between 10 and 45 degrees relative to the sealing surface 232, wherein, in response to the plurality of rows of blood extraction slits being produced, blood components are guided to flow from an opening in the sealing surface through the low-resistance non-microfluidic blood flow channel to the transfer module via the angled transfer port.

Clause 2. The apparatus according to any of the preceding clauses, wherein the lengthwise sliding motion 238 of the slide latch 136 is in a direction of blood flow from the collection site 120 towards the angled transfer port 244.

Clause 3. The apparatus according to any of the preceding clauses, wherein in response to the slide latch 136 being actuated by the lengthwise sliding motion 238, an actuation indicator 130 is configured to visually indicate that the blood collection module 102 has been actuated.

Clause 4. The apparatus according to any of the preceding clauses, wherein in response to the slide latch 136 being actuated by the lengthwise sliding motion 238, an actuation indicator 130 is configured to haptically indicate that the blood collection module 102 has been actuated.

Clause 5. The apparatus of according to any of the preceding clauses, wherein in response to the slide latch 136 being actuated by the lengthwise sliding motion 238, the precompressed volume expansion spring 210 is released causing a partial vacuum to be generated and reduced air pressure to be equalized within the vacuum generation chamber 208, the blood extraction chamber 216, and the transfer module 104 to facilitate rapid blood flow to the transfer module 104.

Clause 6. The apparatus of according to any of the preceding clauses, wherein application of the partial vacuum to the blood extraction chamber 216 causes selected blood extraction slits 278 that are between other blood extraction slits 278 to widen to enhance blood flow.

Clause 7. The apparatus of according to any of the preceding clauses, wherein the plurality of linearly-arranged lancets strips 242 are configured to cause the plurality of rows of blood extraction slits 278 in the skin 122 to be generally aligned with a blood flow direction from the blood collection module 102 to the transfer module 104 to inhibit flow interference from edges of the blood extraction slits 278.

Clause 8. The apparatus of according to any of the preceding clauses, wherein the angled transfer port 244 is configured to fluidically seal around an outside perimeter of the transfer module 104.

Clause 9. The apparatus of according to any of the preceding clauses, wherein the blood collection module 102 is sealed to the skin 122 around the collection site 120 with the transfer module 104 being coupled to the blood collection module 102 lower than the collection site 120 to facilitate self-venting of the low-resistance non-microfluidic blood flow channel 246.

Clause 10. The apparatus of according to any of the preceding clauses, wherein an inner surface 243 of the low-resistance non-microfluidic blood flow channel 246 comprises a blood flow facilitation agent 306 that is a blood flow lubricant 245.

Clause 11. The apparatus of according to any of the preceding clauses, wherein at least a portion of the linearly-arranged lancet strips 242 and/or the low-resistance non-microfluidic blood flow channel 246 of the blood collection module 102 comprise one or more blood flow facilitation agents 306 selected from a vasodilator 309, an anticoagulant 308, and/or a blood flow facilitation agent 306 that is a blood flow lubricant 245.

Clause 12. The apparatus of according to any of the preceding clauses, wherein with the transfer module 104 being coupled to the blood collection module 102 and disposed perpendicularly to a support surface, the angled transfer port 244 causes the opening 235 in the sealing surface 232 of the blood collection module 102 to face at least partially upward to inhibit blood residue from spilling from the opening 235 during decoupling of the transfer module from the angled transfer port 244.

Clause 13. The apparatus of according to any of the preceding clauses, wherein a maximum length of the low-resistance non-microfluidic blood flow channel 246 is less than a minimum inner diameter of the transfer module 104.

Clause 14. The apparatus of according to any of the preceding clauses, wherein an inner minimum cross-sectional area of the low-resistance non-microfluidic blood flow channel 246 in the blood collection module 102 is at least 30% as large as the minimum inner cross-sectional area of the transfer module 104 through which blood 126 collected using the blood collection module 102 is configured to flow.

Clause 15. The apparatus of according to any of the preceding clauses, wherein an inner minimum cross-sectional area of the low-resistance non-microfluidic blood flow channel 246 is within a range of from about 0.2 cm2 to about 0.5 cm2.

Clause 16. A system for accelerated ergonomic collection of capillary blood, the system comprising: a blood collection module 102 that includes: a sealing surface 232 at a subject-facing surface of a base 252 of the blood collection module 102 configured to stably couple to a collection site 120 in skin 122 on a body part 117 of a subject 116, wherein an opening 235 in the sealing surface 232 forms a perimeter through which tips of a plurality of linearly-arranged lancet strips 242 pass, the opening 235 being fluidically coupled to a low-resistance non-microfluidic blood flow channel 246; a slide latch 136 configured to cause the plurality of linearly-arranged lancet strips 242 to momentarily puncture and retract to produce a plurality of rows of blood extraction slits 278 in the collection site 120 in the skin 122 of the subject 116; and an angled transfer port 244 that extends outward from the blood collection module 102 and is angled away from the subject 116 at an acute angle of between 10 and 45 degrees relative to the sealing surface 232 and is configured to couple to a proximal end 203 of the transfer module 104, and wherein, in response to the plurality of rows of blood extraction slits 278 being produced, blood 126 is guided to flow from the opening 235 through the low-resistance non-microfluidic blood flow channel 246 to the transfer module 104 via the angled transfer port 244, wherein the transfer module 104 comprises: a transfer opening 402 at the proximal end 203 of the transfer module 104, e.g., the microtube 105, with an inner diameter of about 10 mm and an outer diameter of about 13 mm; and a prepackaged additive selected to mix with the capillary blood to facilitate performance of one or more predetermined laboratory tests.

Clause 17. The system according to any of the preceding systems clauses, further comprising: an NFC tag 135 coupled to an interior surface of the blood collection module 102; and a process tracking module 108 implemented at least partially on a processor 504 of a portable electronic device 110 and configured to perform a biometric scan to confirm subject identity within a predetermined time period that also includes scanning the NFC tag 135 using the portable electronic device 110.

Clause 18. The system according to any of the preceding systems clauses, further comprising a plasma separation module configured to: receive collected blood from the transfer module decoupled from the blood collection module; and separate cellular blood components from blood plasma.

Clause 19. The system according to any of the preceding systems clauses, wherein the plasma separation module 106 comprises a multilayer laminate 414 below a top plate 412 and above a base plate 438 of the plasma separation module 106 and is configured to perform blood processing to facilitate efficient plasma separation.

Clause 20. The system according to any of the preceding systems clauses, wherein the multilayer laminate 414 comprises: an upper thin film adhesive 416 with a blood-spreading channel 418 that passes through the upper thin film adhesive 416 so as to facilitate even spreading of the blood 126 across a length of the blood-spreading channel 418; and ac.

Clause 21 A method comprising: coupling a blood collection module 102 to a collection site 120 in skin 122 of a subject 116; triggering a momentary puncture and retraction to produce a plurality of rows of blood extraction slits 278 at the collection site 120 by a lengthwise sliding motion 238 of a slide latch 136 of the blood collection module 102 towards a transfer port 244; and transferring blood components from an opening 235 of the blood collection module 102 to a transfer module 104 coupled to the transfer port 244.

Clause 22. The method according to any of the preceding method clauses, further comprising: performing a biometric scan to confirm identity of subject 116 in a usage session that includes collection of the blood 126 from the subject 116.

Clause 23. The method according to any of the preceding method clause, further comprising: scanning 802 an NFC tag 135 coupled to one or more modules used for performing a blood collection; communicating one or more blood collection parameters 605 to a person performing the blood collection; and receiving an indication from the person indicating whether the blood collection was performed according to instructions consistent with the one or more blood collection parameters 605.

Clause 24. The method according to any of the preceding method clauses, further comprising: applying a blood flow facilitation agent 306 comprising an anticoagulant 308 and/or a vasodilator 309 to one or more of: a plurality of linearly-arranged lancet strips 242; a low-resistance non-microfluidic blood flow channel 246 within the blood collection module 102; and the collection site 120 in the skin 122 of the subject 116.

Clause 25. The method according to any of the preceding method clause, wherein the blood flow facilitation agent 306 comprises lidocaine 312.

What is claimed is:
1. An apparatus comprising:
   a blood collection module comprising:
      a proximal portion comprising a vacuum generation chamber formed in a base, a vacuum piston, a precompressed volume expansion spring, and an enclosure with a slot for a slide latch in a top surface of the enclosure relative to the base;
      a distal portion comprising a blood collection chamber formed in the base and configured to collect blood from a collection site in skin of a subject;
      a concave mid portion formed in the enclosure between the proximal portion and the distal portion of the enclosure to facilitate secure holding of the blood collection module between two digits of a hand, the concave mid portion further comprising a pressure equalization channel formed in the base and config- ured to distribute reduced air pressure generated within the vacuum generation chamber to the blood collection chamber, and to a transfer module when the transfer module is coupled to the blood collection module;

a sealing surface at a bottom surface of the base that is configured to stably seal the blood collection module to the skin around the collection site;

a lancet carrier disposed within the distal portion and comprising a plurality of linearly-arranged lancet strips;

the slide latch with a top portion comprising a tab that protrudes up through the slot and a bottom portion of the slide latch comprising a plurality of blocking elements that unblock an upward expansion relative to the base, of a precompressed collar spring and of the precompressed volume expansion spring in response to repositioning of the plurality of blocking elements via a sliding motion of the slide latch, wherein, in response to a sliding motion of the tab of the slide latch through the slot to a first predetermined distance in a distal direction the precompressed collar spring is unblocked from expanding upward relative to the base, and in response triggers a lancet carrier spring to fire the lancet carrier with the plurality of linearly-arranged lancet strips to momentarily puncture and retract from a plurality of rows of blood extraction slits in the skin of the subject at the collection site, wherein, in response to a sliding motion of the tab of the slide latch through the slot to a second predetermined distance in the distal direction, the precompressed volume expansion spring that biases the vacuum piston is unblocked from expanding upward relative to the base and in response begins a vacuum generation of the reduced air pressure within the vacuum generation chamber that is distributed to the blood collection chamber, and to the transfer module when the transfer module is coupled to the blood collection module; and an angled transfer port disposed at the distal portion of the blood collection module and configured to allow the blood to flow from the collection site through a non-microfluidic blood flow channel with greater than submillimeter channel dimensions to the transfer module when coupled, the angled transfer port extending outward from the blood collection module and being angled away from the subject at an acute angle of between 10 and 45 degrees relative to the sealing surface that seals the base to the skin of the subject such that when the transfer module is coupled, an outer wall of the transfer module is also angled away from the skin of the subject at the acute angle of between 10 and 45 degrees relative to the sealing surface, wherein, in response to the plurality of rows of blood extraction slits being produced, the blood and components therein are guided to flow from an opening in the sealing surface through the non-microfluidic blood flow channel to the transfer module when coupled via the angled transfer port.

2. The apparatus of claim 1, wherein a selected relative timing of firing of the plurality of linearly-arranged lancet strips to the vacuum generation triggered by the sliding motion of the slide latch in the distal direction is mechanically selectable by configuring the blood collection module to use a selected slide latch wherein the plurality of blocking elements comprise:

extraction collar blocking elements positioned on the bottom portion of the slide latch at first distances according to the selected relative timing to unblock a collar biased by the precompressed collar spring to trigger the lancet carrier spring to fire the plurality of linearly-arranged lancet strips in response to the sliding motion of the slide latch in the distal direction to the first predetermined distance; and vacuum piston blocking elements positioned on the bottom portion of the slide latch at second positions according to the selected relative timing to unblock the precompressed volume expansion spring to trigger the vacuum generation in response to the sliding motion of the slide latch in the distal direction to the second predetermined distance.

3. The apparatus of claim 1, wherein in response to the slide latch being actuated by the sliding motion in the distal direction, an actuation indicator with a different color from the slide latch is configured to spring through an opening in a top surface of the enclosure to visually indicate that the blood collection module has been actuated.

4. The apparatus of claim 1, wherein in response to the slide latch being actuated by the sliding motion in the distal direction, an actuation indicator is configured to spring through an opening in a top surface of the enclosure to haptically indicate that the blood collection module has been actuated.

5. The apparatus of claim 1, wherein the plurality of linearly-arranged lancet strips comprises two rows of 3 to 6 linearly-arranged lancets per row configured with distal ends of the two rows of linearly-arranged lancet strips being spaced closer together than proximal ends of the two rows of linearly-arranged lancet strips.

6. The apparatus of claim 5, wherein the reduced air pressure distributed to the blood collection chamber causes selected blood extraction slits that are not at respective ends of the two rows of blood extraction slits to widen to enhance blood flow.

7. The apparatus of claim 5, wherein the plurality of linearly-arranged lancet strips are configured to cause a longest dimension of the blood extraction slits of the two rows of blood extraction slits in the skin to be aligned with the two rows of blood extraction slits to guide the blood as it flows from individual blood extraction slits to flow along corresponding rows of blood extraction slits and then flow together as the blood flows in the distal direction from the blood collection module to the transfer module.

8. The apparatus of claim 1, wherein the angled transfer port is configured to fluidically seal around an outside perimeter of the transfer module when coupled.

9. The apparatus of claim 1, wherein the blood collection module is sealed to the skin around the collection site with a vertical orientation in which the proximal portion of the blood collection module is oriented above the distal portion of the blood collection module when the transfer module being is coupled to the angled transfer port of the blood collection module from a direction lower than the collection site to facilitate self-venting, wherein, in the vertical orientation, a portion of the non-microfluidic blood flow channel defined by an interior surface of the angled transfer port comprises:
a gravity-assisted blood flow path along a sub-portion of the non-microfluidic blood flow channel to which the blood is pulled by gravity; and a self-venting return path for air above the gravity-assisted blood flow path.

10. The apparatus of claim 1, wherein at least a portion of the plurality of linearly-arranged lancet strips comprise one or more blood flow facilitation agents selected from a vasodilator and/or an anticoagulant.

11. The apparatus of claim 1, wherein with the transfer module being coupled to the blood collection module and disposed perpendicularly to a support surface, the angled transfer port causes the base comprising the opening in the sealing surface of the blood collection module is angled to face at least partially upward at the acute angle of 10 to 45 degrees relative to the support surface to inhibit blood residue from spilling from the opening during decoupling of the transfer module from the angled transfer port.

12. The apparatus of claim 1, wherein a maximum length of the non-microfluidic blood flow channel defined from a distal edge of the opening in the sealing surface on the blood collection module to a proximal end of the transfer module when coupled is less than 10 mm±10%.

13. The apparatus of claim 1, wherein an inner minimum cross-sectional area of the non-microfluidic blood flow channel is within a range of from 0.2 $cm^2$±10% to 0.5 $cm^2$±10%.

14. A system for accelerated ergonomic collection of capillary blood, the system comprising:
a transfer module; and
a blood collection module that includes:
a sealing surface at a subject-facing surface of a base of the blood collection module configured to stably couple to a collection site in skin on a body part of a subject, wherein an opening in the sealing surface forms a perimeter through which tips of a plurality of linearly-arranged lancet strips pass, the opening being fluidically coupled to a non-microfluidic blood flow channel;
a slide latch configured to cause the plurality of linearly-arranged lancet strips to momentarily puncture and retract to produce a plurality of rows of blood extraction slits in the collection site in the skin of the subject, wherein the plurality of linearly-arranged lancet strips comprises two rows of 3 to 6 linearly-arranged lancets per row configured with distal ends of the two rows of linearly-arranged lancet strips being spaced closer together than proximal ends of the two rows of linearly-arranged lancet strips that are configured to orient a longest dimension of the blood extraction slits of the two rows of blood extraction slits in the skin to be aligned with the two rows of blood extraction slits to guide blood from individual blood extraction slits to flow along corresponding rows of blood extraction slits and then to flow together in a distal direction toward the transfer module; and
an angled transfer port that extends in a distal direction from the blood collection module and is angled away from the skin of the subject at an acute angle of between 10 and 45 degrees relative to the sealing surface and is configured to couple an outer wall of the transfer module to also be angled away from the skin of the subject at the acute angle of between 10 and 45 degrees relative to the sealing surface when the transfer module is coupled to the blood collection module,
wherein, in response to the plurality of rows of blood extraction slits being produced, the blood is guided to flow from the opening through the non-microfluidic blood flow channel to the transfer module via the angled transfer port,
wherein the transfer module comprises a prepackaged additive selected to mix with the blood to facilitate performance of one or more predetermined laboratory tests.

15. The system of claim 14, further comprising:
an NFC tag coupled to an interior surface of the blood collection module; and
a process tracking module implemented at least partially on a processor of a portable electronic device and configured to perform a biometric scan using a camera or a fingerprint scanner of the portable electronic device to confirm subject identity within a predetermined time period that also includes scanning the NFC tag using the portable electronic device to receive information specific to the blood collection module being scanned.

16. The system of claim 14, further comprising a plasma separation module configured to separate plasma from the blood collected from the blood collection module using a multilayer laminate, wherein the multilayer laminate comprises:
a first layer with a blood-spreading channel that facilitates even spreading of the blood across a length of the blood-spreading channel at a center portion of a plasma separation membrane;
a second layer comprising the plasma separation membrane;
a third layer comprising an opening configured for passage of the plasma; and
a fourth layer comprising a plasma collecting plate configured to provide multiple open spaces through which the plasma can flow as it moves towards an outlet hole to pass through the plasma collecting plate to be dispensed.

17. A method comprising:
coupling a blood collection module to a collection site in skin of a subject;
coupling a transfer module to an angled transfer port of the blood collection module such that an outer wall of the transfer module is angled away from the skin of the subject at an acute angle of between 10 and 45 degrees relative to a sealing surface at a bottom surface of a base of the blood collection module that seals the base to the skin of the subject around the collection site;
sliding a slide latch of the blood collection module with a mechanically selected timing of lancet firing relative to vacuum generation based on relative positioning of blocking elements on a bottom portion of the slide latch in a distal direction towards the angled transfer port to perform:
triggering a momentary lancet strip puncture and retraction at the collection site to produce two rows of 3 to 6 blood extraction slits per row at the collection site to guide blood to flow along the two rows of blood extraction slits, wherein distal ends of the two rows of blood extraction slits are closer together than proximal ends of the two rows of blood extraction slits; and
triggering, with timing relative to the momentary lancet strip puncture and retraction based on the relative positioning of the blocking elements of the slide latch, a distribution of reduced air pressure to facilitate extraction of the blood and components therein from the collection site; and transferring the blood and components therein from an opening of the blood collection module to the transfer module coupled to the angled transfer port.

\* \* \* \* \*